US009616110B2

(12) United States Patent
Neu et al.

(10) Patent No.: US 9,616,110 B2
(45) Date of Patent: Apr. 11, 2017

(54) FABRICATION METHOD FOR STRATIFIED AND LAYERED TISSUE TO REPAIR OSTEOCHONDRAL DEFECTS

(71) Applicant: Purdue Research Foundation, West Lafayette, IN (US)

(72) Inventors: Corey P. Neu, West Lafayette, IN (US); Tyler A. Novak, Lafayette, IN (US); Garrett Shannon, Milwaukee, WI (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/194,207

(22) Filed: Feb. 28, 2014

(65) Prior Publication Data

US 2014/0242140 A1 Aug. 28, 2014

Related U.S. Application Data

(60) Provisional application No. 61/770,882, filed on Feb. 28, 2013.

(51) Int. Cl.
*A61K 38/39* (2006.01)
(52) U.S. Cl.
CPC .................................. *A61K 38/39* (2013.01)
(58) Field of Classification Search
CPC ....................................................... A61K 38/39
See application file for complete search history.

(56) References Cited

U.S. PATENT DOCUMENTS

| 6,387,693 B2 | 5/2002 | Rieser et al. | |
|---|---|---|---|
| 2010/0074874 A1* | 3/2010 | Torbet et al. | 424/93.7 |
| 2012/0015003 A1* | 1/2012 | Gleeson et al. | 424/400 |

OTHER PUBLICATIONS

Franklin T. Moutos, et al., "A Biomimetic Three-Dimensional . . . of Cartilage", Nature Materials, Feb. 2007, pp. 162-167, vol. 6, Nature Publishing Group, Duke University Medical Center, Durham, NC.
Mats Brittberg, M.D., et al., "Treatment of Deep Cartilage . . . Transplantation", The New England Journal of Medicine, Oct. 6, 1994, vol. 331, No. 14, pp. 889-895, Massachusetts Medical Society, MA.
A.H. Reddi, "Cartilage-Derived Morphogeneticc . . . Morphogenesis", Microscopy Research and Technique, vol. 43, 1998, pp. 131-136, Wiley-Liss, Inc., University of California Davis, School of Medicine, Sacramento, CA.
C.P. Neu, et al., "Characterization of Engineered . . . Resonance Imaging", Journal of Tissue Engineering and Regenerative Medicine, 2009, vol. 3, pp. 477-485, John Wiley & Sons, Ltd., University of California Davis, School of Medicine, Sacramento, CA.
C.P. Neu, et al., "MRI-Based Technique for Determining . . . Explants", Magnetic Resonance in Medicine, 2005, vol. 53, pp. 321-328, Wiley-Liss, Inc., University of California Davis, School of Medicine, Sacramento, CA.
C.P. Neu, et al., "Mechanotransduction of Bovine . . . Factor B Signaling", Arthritis & Rheumatism, Nov. 2007, vol. 56, No. 11, pp. 3706-3714, American College of Rheumatology, University of California Davis, School of Medicine, Sacramento, CA.
C.P. Neu, et al., "The Interface of Functional Biotribology . . . Synovial Joints", Tissue Engineering, 2008, vol. 14, No. 3, pp. 235-247, University of California Davis, School of Medicine, Sacramento, CA.
Jared J. Diegmueller, et al., "Modulation of Hydroxyapatite . . . Peptides", Crystal Growth & Design, 2009, vol. 9, pp. 5220-5226, American Chemical Society, Purdue University, West Lafayette, IN.
Frank P. Luyten, et al., "Recombinant Bone Morphogenetic Protein-4, . . . Chondrocytes in Vitro", Experimental Cell Research, 1994, vol. 210, pp. 224-229, Academic Press, MD.
Afshin Khalafi, et al., "Increased Accumulation of Superficial . . . Growth Factors", Journal of Orthopaedic Research, Mar. 2007, pp. 293-303, Wiley Interscience, University of California Davis, School of Medicine, Sacramento, CA.
Van C. Mow, et al., "Cartilage and Diarthrodial Joints . . . and Structures", Biomaterials, 1992, vol. 13, No. 2, pp. 67-97, Butterworth-Heinemann Ltd., Columbia University, NY.
J.G. Ramasamy, et al., "Local Variations in the Micromechanical . . . and Mineralization", Journal of Biomechanics, 2007, vol. 40, pp. 910-918, Elsevier, Toledo, OH.
G.A. Dunn, et al., "Contact Guidance on Oriented Collagen Gels", Exp Cell Res, 1978, vol. 111, pp. 475-479, Cambridge, UK.
Tom Elsdale, et al., "Collagen Substrata for Studies on Cell Behavior", The Journal of Cell Biology, 1972, vol. 54, pp. 626-637, Edinburgh, Scotland.
P.C. Wilkinson, et al., "Contact Guidance of Human Neutrophil Leukocytes", Experimental Cell Research, 1982, vol. 140, pp. 55-62, Academic Press, Inc., University of Glasgow, Scotland.
Susan Liao, et al., "Biomimetic Electrospun Nanofibers for Tissue Regeneration", Biomedical Materials, 2006, vol. 1, pp. R45-R53, Institute of Physics Publishing, National University of Singapore, Singapore.
Dimitrios I. Zeugolis, et al., "Electro-spinning of Pure Collagen . . . To Make Gelatin?", Biomaterials, 2008, vol. 29, pp. 2293-2305, Elsevier Ltd., Singapore.
Xingguo Cheng, et al., "An Electrochemical Fabrication . . . Collagen Bundles", Biomaterials, 2008, vol. 29, pp. 3278-3288, Elsevier Ltd., Purdue University, Lafayette, IN.

(Continued)

*Primary Examiner* — Gina Justice
(74) *Attorney, Agent, or Firm* — Reichel Stohry LLP; Natalie J. Dean; Mark C. Reichel

(57) ABSTRACT

Fabrication method for stratified and layered tissue to repair osteochondral defects. In a method of the present disclosure, the method comprises the step of applying a first direction magnetic field to a first quantity of a first collagen solution to align collagen within the first collagen solution in a first direction relative to the first direction magnetic field, forming a first layer of collagen. In a method of generating an aligned collagen layer of the present disclosure, the method comprises applying a first magnetic field at or greater than 0.1 Tesla to a layer of a first collagen solution defining a horizontal plane, within a temperature at or between 2° C. and 45° C., to generate an aligned collagen layer.

20 Claims, 29 Drawing Sheets

(56) References Cited

OTHER PUBLICATIONS

Jim Torbet, et al., "Orthogonal Scaffold of Magnetically . . . Stroma Reconstruction", Biomaterials, 2007, vol. 28, pp. 4268-4276, Elsevier Ltd., Lyon, France.

R.T. Tranquillo, et al., "Magnetically Orientated Tissue-Equivalent . . . Media-Equivalent", Biomaterials, 1996, vol. 17, No. 3, pp. 349-357, Elsevier, University of Minnesota, Minneapolis, MN.

J.S. Pieper, et al., "Crosslinked Type II Collagen . . . Cartilage Engineering", Biomaterials, 2002, vol. 23, pp. 3183-3192, Elsevier Science Ltd., Nijmegen, The Netherlands.

P. Julkunen, et al., "Biomechanical, Biochemical and . . . Articular Cartilage", Osteoarthritis and Cartilage, 2009, vol. 17, pp. 1628-1638, Osteoarthritis Research Society International, Elsevier Ltd., Kuopio, Finland.

Brian O. Diekman, B.S., et al., "Chondrogenesis of Adult Stem Cells . . . Cartilage-Derived Matrix", Tissue Engineering, 2010, vol. 16, No. 2, pp. 523-534, Duke University Medical Center, Durham, NC.

Grayson DuRaine, et al., "Regulation of the Friction Coefficient . . . and IL-1B", Journal of Orthopaedic Research, Feb. 2008, pp. 249-256, Wiley InterScience, University of California Davis, Sacramento, CA.

Elizaveta, Kon, et al., "Orderly Osteochondral Regeneration . . . Multilayered Biomaterial", Orthopaedic Research Society, Jan. 2010, Vol .28, pp. 116-124, Wiley Periodicals, Inc., Bologna, Italy.

N. Dubey, et al., "Guided Neurite Elongation and Schwann . . . Nerve Regeneration", Experimental Neurology, 1999, vol. 158, pp. 338-350, Academic Press, Minneapolis, MN.

Xingguo Cheng, et al., "An Electrochemical Fabrication . . . Collagen Bundles", Biomaterials, 2008, vol. 29, pp. 3278-3288, Elsevier Ltd., Purdue University, West Lafayette, IN.

Howard A. Breinan, et al., "Effect of Cultured Autologous . . . in a Canine Model", The Journal of Bone and Joint Surgery, 1997, vol. 79-A, No. 10, pp. 1439-1451, Harvard Medical School, Boston, MA.

\* cited by examiner

FABRICATION METHOD FOR STRATIFIED AND LAYERED TISSUE TO REPAIR OSTEOCHONDRAL DEFECTS

PRIORITY

The present U.S. nonprovisional application is related to, and claims the priority benefit of, U.S. provisional patent application Ser. No. 61/770,882, filed Feb. 28, 2013, the contents of which are hereby incorporated into the present disclosure in their entirety.

TECHNICAL FIELD

The present disclosure generally relates to tissue engineering.

BACKGROUND

This section introduces aspects that may help facilitate a better understanding of the disclosure. Accordingly, these statements are to be read in this light and are not to be understood as admissions about what is or is not prior art.

The treatment of osteoarthritis (OA), a degenerative joint disease affecting more than 40% of U.S. adults and an economic burden annually exceeding $65 billion, is an unmet need in medicine. A hallmark of OA is the progressive wear of articular cartilage, the primary joint bearing material that facilitates smooth, pain-free movement. The treatment of cartilage/bone (osteochondral) defects, leading to OA in the long term, is challenging because the tissue is intrinsically recalcitrant to repair, partly due to its avascularity and slow cellular turnover. Moreover, cartilage has a stratified (zonal) structure with spatial gradients in collagen alignment and localized protein expression. In recent years, Tissue engineering-based methods have shown promise to repair defects, but none is able to recapitulate the native structure of cartilage, and the typical end-point for diseased tissue is biomechanically-inferior fibrous repair tissue and/or total joint arthroplasty.

Collagen, the main structural protein found in the connective tissue of animals, can be aligned using a variety of techniques. Scaffolds with isotropically-oriented fibrils exhibit poor mechanical strength in specific and functionally-important directions. Anisotropic collagen scaffolds closely resemble the natural articular cartilage environment and promote cellular migration and growth, possibly due to alignment of focal adhesions and haptotaxis. Drainage-induced orientation is a process by which collagen solution is precipitated into bundles and placed on an inclined surface to align the fibers. The stretch-induced orientation method involves a fluid absorption process that contracts collagen. Both these methods have very low reproducibility with nonuniform fibril orientation. Electrospinning uses electrical fields to produce oriented collagen fibers. This technology has shown promise for creating continuous two dimensional fibers useful for skin and tendon regeneration, however this process also denatures collagen. A separate electrochemical process attains high degree of two dimensional collagen fiber orientation for tendon/ligament replacement. This process is carried out in distilled water and requires low electric voltage and current. However, it is unclear whether electrospinning and electrochemical processes are capable of creating complex three-dimensional and zonal architecture required for osteochondral scaffolds.

Existing scaffolds do not have zonal collagen alignment that match the osteochondral structure of cartilage and bone. Additionally, existing collagen-derived scaffolds exhibit an inferior mechanical stiffness, and are thus unsuitable for long-term repair success.

The repair and regeneration of articular cartilage is challenging. Unfortunately, there is no product or surgical strategy that results in reproducibly healthy tissue. Several traditional techniques of cartilage repair are based on accessing the subchondral vascularity and marrow by drilling of the subchondral bone, spongialization, or microfracturing. A common result of these techniques is a fibrocartilage-like repair tissue developed with inferior composition, structure, and mechanical properties compared to normal cartilage.

Autologous chondrocyte transplantation (ACT) is a current "gold standard" of practice for the repair of deep cartilage defects. ACT involves the reintroduction of expanded autologous cells into a surface defect, although results are highly variable.

Therefore, there is a need for the ability to engineer complex and native zonal structure of cartilage and bone in order to restore depth-dependent properties and normal mechanical function.

BRIEF SUMMARY

The present disclosure provides methods for treatment of osteoarthritis and osteochondral defects, including methods of generating desired collagen-based constructs.

In at least one embodiment of a method of the present disclosure, the method comprises the step of applying a first direction magnetic field to a first quantity of a first collagen solution to align collagen within the first collagen solution in a first direction relative to the first direction magnetic field, forming a first layer of collagen. In at least one embodiment of a method of generating an aligned collagen layer of the present disclosure, the method comprises applying a first magnetic field at or between 0.1 Tesla to 15.0 Tesla (or at or greater than 0.1 Tesla) to a layer of a first collagen solution defining a horizontal plane, within a temperature at or between 2° C. and 45° C., to generate an aligned collagen layer. Collagen fibers within the aligned collagen layer, or as referenced herein, within one or more additional collagen layers that are aligned using a magnetic field, can be aligned within an orientation angle range of plus or minus 10 degrees, meaning that the collagen fibers have an average/mean direction and a deviation of plus or minus 10 degrees. Additional alignment angle ranges, such as plus or minus 20, 30, 40, 50, 60, or 70 degrees, for example, are also contemplated herein. In various embodiments, the step of applying is performed at a temperature at or between 12° C. and 37° C., at a temperature at or between 10° C. and 25° C., or at a temperature at or between 15° C. and 18° C. In various exemplary embodiments, the step of applying is performed at or about 12° C., 18° C., 20° C., 25° C., or 37° C., or at a temperature at or between above 0° C. and 25° C. In several embodiments, the first magnetic field is applied at a direction selected from the group consisting of a direction of the horizontal plane and a direction perpendicular to the horizontal plane, such as a relative 0° direction or a 90° direction relative to the horizontal plane. Furthermore, the first layer of collagen (or the aligned collagen layer) may be formed using one or more additional solutions, with or without collagen, in addition to the first collagen solution. For example, an exemplary first layer (aligned collagen layer) can comprise the first quantity of the first collagen solution along with one or more additional liquids or solutions.

In at least one embodiment of a method of the present disclosure, the method further comprises the step of combining the first layer of collagen (or the aligned collagen layer) with a second layer of collagen, the second layer of collagen comprising a quantity of a collagen solution selected from the group consisting of a first quantity of a second collagen solution and a second quantity of the first collagen solution, wherein the second layer of collagen is positioned adjacent to the first layer of collagen (or the aligned collagen layer), forming a construct. In various embodiments, the step of combining is performed at a temperature at or between 2° C. and 45° C., at a temperature at or between 12° C. and 37° C., or at a temperature at or between 10° C. and 25° C. In various exemplary embodiments, the step of combining is performed at or about 12° C., 18° C., 20° C., 25° C., or 37° C., or at a temperature at or between above 0° C. and 25° C. Furthermore, the second layer of collagen may also be formed using one or more additional solutions, with or without collagen, in addition to the second collagen solution. For example, an exemplary second layer can comprise the first quantity of the second collagen solution and/or the second quantity of the first collagen solution along with one or more additional liquids or solutions.

In at least one embodiment of a method of the present disclosure, the step of combining further comprises the step of applying a magnetic field selected from the group consisting of the first magnetic field and a second magnetic field to the second layer of collagen to align collagen within the second layer of collagen relative to the selected magnetic field. In various embodiments, the method further comprises the step of further combining the first layer of collagen (or the aligned collagen layer) and the second layer of collagen with a third layer of collagen, the third layer of collagen comprising a quantity of a collagen solution selected from the group consisting of the first quantity of the second collagen solution, a second quantity of the second collagen solution, the second quantity of the first collagen solution, a third quantity of the first collagen solution, and a first quantity of a third collagen solution, wherein the third layer of collagen is positioned adjacent to one or both of the first layer of collagen (or the aligned collagen layer) and the second layer of collagen, adding to the construct. Said step can be performed at any of the aforementioned temperatures or temperature ranges, and can include one or more additional liquids or solutions in addition to the chosen solution. In various embodiments, the step of further combining further comprises the step of applying a magnetic field selected from the group consisting of the first magnetic field, the second magnetic field, and a third magnetic field to the third layer of collagen to align collagen within the third layer of collagen relative to the selected magnetic field. In several embodiments, the method further comprises the step of adding one or more layers of a collagen solution to the construct.

In at least one embodiment of a method of the present disclosure, the first collagen solution comprises collagen and at least one substance selected from the group consisting of one or more minerals, one or more proteoglycans, hydroxyapatite, calcium, phosphorous, a combination of calcium and phosphorous, aggrecan, chondroitin sulfate, dermatan sulfate, genepin, hyaluronic acid, 1-Ethyl-3-(3-dimethylaminopropyl)carbodiimide, one or more cells, one or more primary mammalian cells, and one or more progenitor mammalian cells (or a combination of any of the foregoing), and wherein the second collagen solution comprises collagen and is at least substantially free of the selected at least one substance. In various other embodiments, the second collagen solution may also comprise the substance as the first collagen solution, a different substance than the first collagen solution, or the same plus a different substance as compared to the first collagen solution. For example, in embodiments used to connect to bone at two ends (such as with ligament replacement/treatment, for example), the outermost layers may have at least one substance, such as a mineral and/or one or more of the foregoing substances. Any of the other collagen solutions or liquids referenced above can also include one or more of the aforementioned substances. In several method embodiments, the first direction magnetic field is at or about 90° relative to the second magnetic field.

In at least one embodiment of a method of the present disclosure, the method further comprises the step of administering at least the first layer of collagen (or the aligned collagen layer) to a patient to treat a condition experienced by the patient, the condition selected from the group consisting of an arthritic condition, a cartilage-based condition, a bone-based condition, a meniscus condition, a blood vessel condition, a ligament condition, a tendon condition, and a skin condition. This administration step, or an additional administration step, can also include administering a construct of the first layer of collagen plus one or more additional layers of collagen within the construct or as a separate construct.

In at least one embodiment of a method of treating a patient of the present disclosure, the method comprises the step of administering a construct to a patient to treat a patient condition, the construct comprising a first layer of collagen formed by applying a first direction magnetic field to a first quantity of a first collagen solution at a temperature of at or between 10° C. and 25° C. to align collagen within the first collagen solution in a first direction relative to the first direction magnetic field. In various methods, the construct is further formed by combining the first layer of collagen with a second layer of collagen, the second layer of collagen comprising a quantity of a collagen solution selected from the group consisting of a first quantity of a second collagen solution and a second quantity of the first collagen solution, wherein the second layer of collagen is positioned adjacent to the first layer of collagen. The aforementioned constructs can be produced at any of the aforementioned temperatures or temperature ranges, and can include one or more additional liquids or solutions in addition to the chosen solution. In several embodiments of the present disclosure, the step of combining further comprises the step of applying a magnetic field selected from the group consisting of the first magnetic field and a second magnetic field to the second layer of collagen to align collagen within the second layer of collagen relative to the selected magnetic field. In various embodiments, the construct is further formed by adding one or more layers of a collagen solution to the construct.

In at least one embodiment of a collagen-based product of the present disclosure, the product comprises a first collagen layer produced by applying a first direction magnetic field to a first quantity of a first collagen solution to align collagen within the first collagen solution in a first direction relative to the first direction magnetic field, wherein the first direction magnetic field is applied to the first collagen solution at a temperature of at or between 10° C. and 25° C. In various embodiments, the product further comprises a second layer of collagen is positioned adjacent to the first layer of collagen, the second layer of collagen comprising a quantity of a collagen solution selected from the group consisting of a first quantity of a second collagen solution and a second quantity of the first collagen solution, wherein a magnetic field selected from the first direction magnetic field and a second direction magnetic field is applied to the second layer at a temperature of at or between 10° C. and 25° C.

The aforementioned products can be produced at any of the aforementioned temperatures or temperature ranges, and can include one or more additional liquids or solutions in addition to the chosen solution. In several product embodiments, the first collagen solution comprises collagen and at least one mineral, and wherein the second collagen solution comprises collagen and is at least substantially mineral-free. In various other embodiments, the second collagen solution may also comprise the substance as the first collagen solution, a different substance than the first collagen solution, or the same plus a different substance as compared to the first collagen solution. For example, in embodiments used to connect to bone at two ends (such as with ligament replacement/treatment, for example), the outermost layers may have at least one substance, such as a mineral and/or one or more of the foregoing substances.

In at least one embodiment of a method of generating an aligned collagen layer of the present disclosure, the method comprises applying a first magnetic field at or between 0.1 Tesla to 15.0 Tesla (or at or greater than 0.1 Tesla) to a layer of a first collagen solution defining a horizontal plane, within a temperature at or between 2° C. and 45° C., to generate an aligned collagen layer; and crosslinking the aligned collagen layer, resulting in an individual aligned crosslinked collagen layer. In various embodiments, the method further comprises the step of combining the aligned collagen layer with a second layer of collagen, the second layer of collagen comprising a quantity of a collagen solution selected from the group consisting of a first quantity of a second collagen solution and a second quantity of the first collagen solution, wherein the second layer of collagen is positioned adjacent to the aligned collagen layer, forming a construct. In several embodiments, the step of combining further comprises the step of applying a magnetic field selected from the group consisting of the first magnetic field and a second magnetic field to the second layer of collagen to align collagen within the second layer of collagen relative to the selected magnetic field. In various embodiments, the method further comprises the step of further combining the aligned collagen layer and the second layer of collagen with a third layer of collagen, the third layer of collagen comprising a quantity of a collagen solution selected from the group consisting of the first quantity of the second collagen solution, a second quantity of the second collagen solution, the second quantity of the first collagen solution, a third quantity of the first collagen solution, and a first quantity of a third collagen solution, wherein the third layer of collagen is positioned adjacent to one or both of the aligned collagen layer and the second layer of collagen, adding to the construct.

In various product embodiments, at least one of the first collagen solution and the second collagen solution comprise at least one substance selected from the group consisting of one or more minerals, one or more proteoglycans, hydroxyapatite, calcium, phosphorous, a combination of calcium and phosphorous, aggrecan, chondroitin sulfate, dermatan sulfate, genepin, hyaluyronic acid, 1-Ethyl-3-(3-dimethylaminopropyl)carbodiimide, one or more cells, one or more primary mammalian cells, and one or more progenitor mammalian cells. Additional product embodiments can comprise additional layers of collagen using any number of the aforementioned solutions.

DETAILED DESCRIPTION

Figure 1:
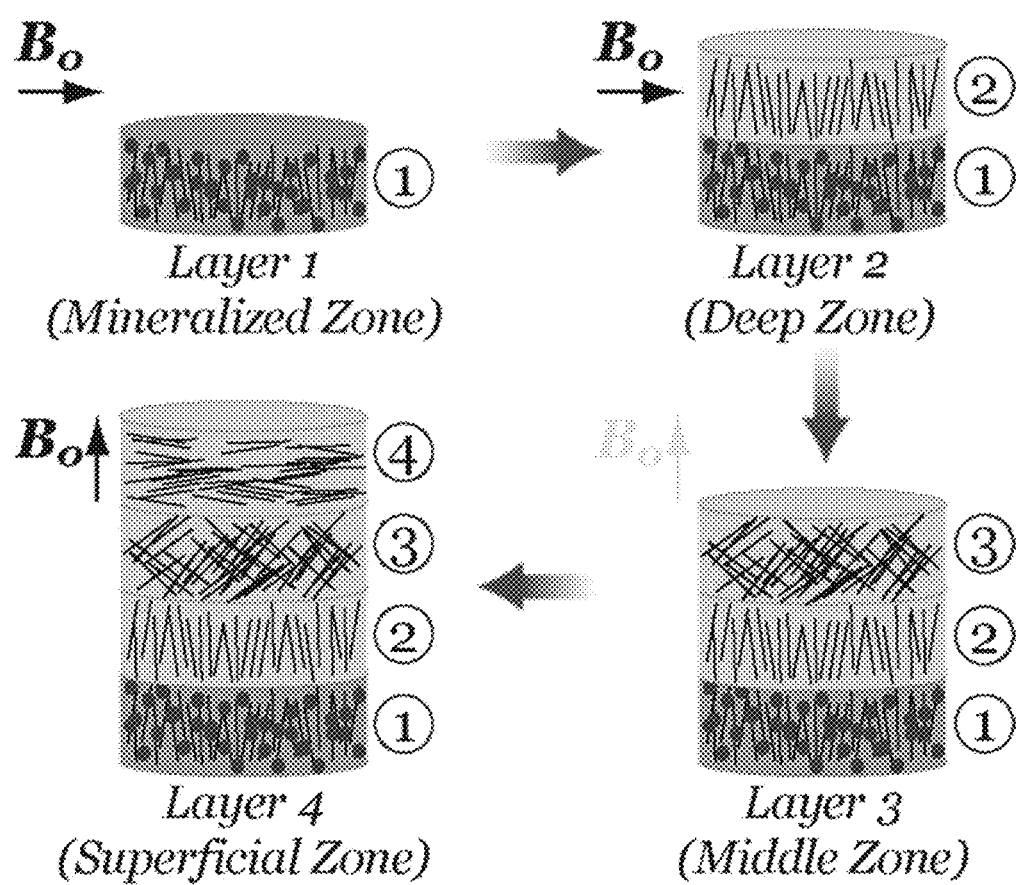
FIG. 1 depicts a schematic for a fabrication process for control of collagen orientation by application of magnetic fields, according to an exemplary embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel fabrication methodology, termed MAgnetic Prototyping in 3D (MAP3D), for the treatment of osteoarthritis and osteochondral defects is described. Through the MAP3D, stratified scaffolds can be generated that closely resemble the zonal ultrastructure of normal osteochondral tissue. As generally referenced herein, such a process can be used to form a construct or product including collagen that can be administered to a patient to treat a condition experienced by the patient, such as an arthritic condition, a cartilage-based condition, a bone-based condition, a meniscus condition, a blood vessel condition, a ligament condition, and a skin condition, as provided in further detail herein.

Alignment of collagen molecules can be attained in the presence of magnetic fields. Concentrated solutions of collagen molecules are influenced by magnetic fields through the diamagnetic anisotropy of planar peptide bonds. Alignment of collagen is not limited to a particular type, and can include both type I or type II collagen or others, noting that type II collagen is the dominant structural molecule in articular cartilage. Collagen fiber, as referenced herein, means any collagen of type I, II, IV, and VI, and existing as a monomer, dimer, trimer, or oligomer. Alpha, beta, and gamma strands are all also included, and the source can be animal (for example human) or synthetic. Collagen fibrils are oriented normal to the direction of the magnetic field. Orthogonally aligned collagen fibrils for corneal reconstruction have been demonstrated. Circumferentially oriented collagen fibrils have been used to design tissue-engineered media equivalents.

The MAP3D process includes a layer-by-layer fabrication process. A noninvasive control of collagen orientation by magnetic fields in conjunction with cells and matrix is incorporated (See FIG. 1). For each layer, the construct may be exposed to an external magnetic field, and/or may be oriented with respect to the field, depending on the ultrastructure required to resemble the tissue. Each layer may additionally be augmented with minerals, matrix, and cells, to tailor the tissue structure and function. Zonal tissue with depth-dependent biomechanical and biochemical characteristics can be expected. Moreover, the MAP3D may be used to align collagen on a molecular scale which can enable unique restoration of osteochondral tissue with tailored macroscale function, and therefore can increase the functional lifespan post-implantation in vivo. The MAP3D process is a significant improvement over existing technologies because it can: (1) provide the first zonal and stratified construct that closely resembles a natural counterpart, (2) minimize (inferior) fibrocartilage repair tissue that typically results from common surgical procedures, (3) serve as a carrier for cells and soluble factors, (4) require simple delivery using existing clinical and surgical procedures, and (5) require low costs to fabricate using an abundantly-available molecule (collagen).

FIG. 1 depicts a schematic for a fabrication process for control of collagen orientation by application of magnetic fields. Collagen is first aligned by an external magnetic field ($B_o$) and augmented by mineral content. A second layer without mineral resembles the deep zone of cartilage. A random collagen layer (middle zone) is added without the magnetic field (note the ghosted $B_o$ field). A final aligned layer (superficial zone) is added after rotating the construct with respect to $B_o$. Specific cell suppopulations may be added during fabrication in each layer.

The MAP3D process can be configured to advantageously repair cartilage defects with zonal MAP3D constructs. MAP3D scaffolds can include multiple zones aligned by magnetic fields (to resemble cartilage ultrastructure) and mineralized (to resemble subchondral bone). The scaffold may then be comprised of type I and type II collagen, and can be crosslinked by genipin or other agents (e.g. 1-Ethyl-3-(3-dimethylaminopropyl)carbodiimide (EDAC)). In certain embodiments, crosslinking is performed by chemical, physical (i.e. pressure), radiative, pH, heat, and/or other processes known in the art. In at least one embodiment, each layer is solely crosslinked as an individual unit. In other embodiments, each layer is crosslinked to the adjacent layer to generate a connected unit of all layers of collagen. In additional embodiments, the layers are held together by attachments to a scaffold made of a material. In other embodiments, the individual layers are held together via a chemical bond (i.e., as a non-limiting example, superglue). In various other embodiments, the layers are held together by a staple or a screw made of a synthetic or metallic material. In certain embodiments, the synthetic or metallic material is biodegradable.

As generally referenced herein, and in at least one exemplary method of generating an aligned collagen layer of the present disclosure, the method comprises applying a first magnetic field at or between 0.1 Tesla to 15.0 Tesla to a layer of a first collagen solution having an alignment angle at or between 0 degrees and 70 degrees relative to an axis perpendicular to a horizontal plane of the layer of the first collagen solution, within a temperature at or between 2° C. and 45° C., to generate an aligned collagen layer. Placing a first collagen solution upon a substrate (such as a laboratory vessel like a dish, slide, cup, etc., on another layer of a collagen solution, or upon another suitable substrate) would result in the defined horizontal plane, such as defined by the surface of the collagen solution, with the axis perpendicular to the horizontal plane being vertical, for example.

Collagen alignment and mineralization can be assessed by birefringence and electron microscopy. Furthermore, primary or progenitor cells can be incorporated in MAP3D scaffolds. Primary cells can be used in light of autologous cartilage transplantation that are used in clinical settings. Progenitor cells can be used considering their use in clinical and differentiation situations. The extent that MAP3D repairs defects in a well-established animal model can also be evaluated. MAP3D tissue can be compared to controls (e.g. unrepaired defects). Functional assessment of repair tissue can include analysis of surface, bulk, and depth-dependent mechanical function. Zonal protein expression and tissue integration can also be evaluated histologically post-sacrifice.

Figure 2:
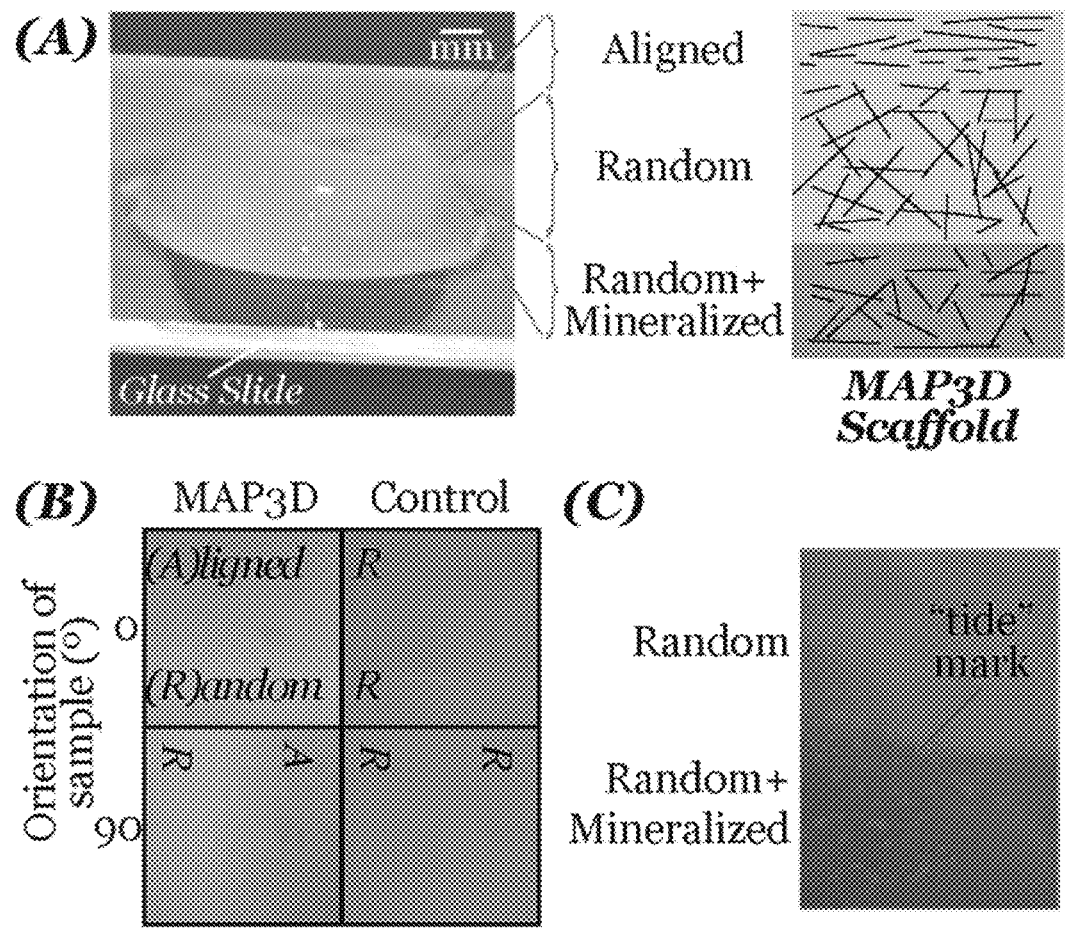
FIG. 2 depicts an exemplary process for MAgnetic Prototyping in 3D (MAP3D) scaffold developed with stratified, aligned, and mineralized collagen layers, according to an exemplary embodiment of the present disclosure.

A proof-of-concept MAP3D construct was developed. FIG. 2 depicts an exemplary process for MAP3D scaffold developed with stratified, aligned, and mineralized collagen layers. Collagen gels were neutralized at 4° C. by adding 8:1:1 of collagen solution: 3 mg/mL bovine hide type I collagen, 0.01M NaOH: 10×DPBS. The pH of the solution was adjusted to 7.4±0.2. Mineralization was accomplished using a Ca/P ratio of 2 to grow hydroxyapatite crystals on the first (Random+Mineralized) layer of the collagen gel. The second (Random) layer was achieved by placing a fresh aliquot of collagen solution in a glass well and allowing to gel without magnetic exposure at 37° C. for one hour. The third layer (Aligned) was achieved by layering a fresh aliquot of collagen solution on top of the random layer and placing the glass well horizontally in the 9.4 Tesla magnet (Chemagnetics) for 1 hour. The scaffolds were then cross-linked (by UV exposure; 254 nm) for 45 minutes. In certain embodiments the magnetic strength is at least 0.1 T or 0.5 T. In other embodiments, the magnetic range is at or between 0.1 T or 0.5 T and 25 T, or at or between 0.5 T and 15 T.

FIG. 3A depicts a series of images of collagen alignment using a superconducting high-field strength magnet. Type I collagen was prepared as described previously to a gel thickness of 3 mm. The gels were placed in the bore center of a 9.4 T superconducting magnet (Chemagnetics CMX400) at 20° C. After a period of 10 minutes the temperature was raised to 37° C. The wells were exposed to the magnetic field for 1 hour. After removal from the magnet, the aligned gels were placed under a UV lamp (254 nm) and cross linked for 45 minutes, and then in a 37° C. air stream incubator for 30 minutes. Non-aligned (random) collagen gels were prepared using the same protocol without the magnetic exposure. Collagen alignment was shown by scanning electron microscopy (SEM) at hierarchical levels. Gels without magnetic field exposure appeared random in orientation at all levels of magnification (1,000-200,000×) in contrast to gels exposed to 9.4 T. Therefore, these data demonstrate the ability to align collagen by magnetic fields.

The response of primary and progenitor cells to a superconducting magnetic was demonstrated using incorporation and viability (Live/Dead), and proliferation (cell count) assays (see FIGS. 3B and 3C). Primary chondrocytes were extracted from the articular cartilage of young bovine knee joints (approximate age of 3 months) by 0.2% collagenase-P for 5 hours. Isolated chondrocytes were cultured or embedded in collagen gels at a high density ($10^6$ cells/1 mL medium) and subsequently cultured (37° C., 5% $CO_2$) in serum-free, chemically-defined low glucose Dulbecco's modified Eagle culture medium: nutrient mixture F12 (Ham) 1:1 (D-MEM/F-12, Invitrogen), supplemented with 0.1% bovine serum albumin, 100 units/ml penicillin, 100 µg/ml streptomycin, and 50 µg/ml ascorbate-2-phosphate and supplemented with 10% FBS. Living cells were seen in both aligned and random gels (FIG. 3B). Proliferation of the cells was unchanged following magnetic field exposure (FIG. 3C). Therefore, these data indicate that primary and progenitor cells may be incorporated into collagen gels during alignment by magnetic fields.

The structure of cartilage and bone is complex. The dominant constituents of normal articulating cartilage are type II collagen (15-22%) and proteoglycans (4-7%) (wet tissue weight). Collagen provides tensile strength whereas proteoglycans, e.g. aggrecan, regulate compressive stiffness. The interaction between these two networks is also known to affect fibrillogenesis and control the overall biology of the tissue. At the ultrastructure level, the collagen fibers in cartilage are distinctly organized in three orientations. In the superficial zone, the fibers run parallel to the surface, whereas in the middle zone the fibers are oblique or random. The deep zone fibers are perpendicular to the surface and anchored into the subchondral bone layer. The collagen and proteoglycan densities are inversely related, with the collagen content being the highest in the superficial zone. This architecture affects the metabolic and synthetic activity of cells. The subchondral bone layer includes mineralized type I collagen.

According to one embodiment of the present disclosure, collagen solution preparation can include neutralizing the collagen solution with DPBS at 4° C. to prepare for fibril formation. Collagen alignment can involve concomitant exposure to a magnetic field and increasing temperature (to 37° C.) to promote fibrillogenesis. Stratified gels can be developed by layering fresh aliquots of collagen solution on top of the aligned gel. The volume of the aliquot will govern the thickness of the layer and will be matched to the thickness of native cartilage. After the first orientation (perpendicularly aligned and mineralized collagen fibers forming a subchondral deep zone layers) is achieved, a fresh aliquot of collagen solution can be added on top and allowed to cure at 37° C. without magnetic exposure to form a random middle zone. Similarly, the third orientation can be achieved by placing a fresh aliquot of collagen solution on the aligned gel and rotating the sample to attain alignment of fibers in the parallel direction. Control (randomly-oriented) gels can include all steps except exposure to the magnetic field. For the bone layer, type I collagen from fetal bovine dermis can be obtained from, e.g. BD Biosciences. Similarly, for the cartilage layer, type II collagen can be obtained commercially (e.g., BD Biosciences) or isolated from porcine or bovine tracheal cartilage. In the latter case, purity can be checked by SDS-PAGE, and treated with pepsin to prepare atelocollagen (collagen without telopeptides) that may properly swell in acetic acid necessary for preparation of matrices. Calcium hydroxyapatite crystals can be custom made (See FIG. 2). Mineralization can be accomplished using a Ca/P ratio of 2 to grow crystals in the collagen gel. Magnetic field exposure time may govern the degree of fibril orientation due to altered diamagnetic anisotropy of the planar peptide bonds, and thus the overall construct fabrication time, as a minimum time is desired in the layer-by-layer process. Gels can be exposed to graded levels (1, 15, 30, and 60 min) of exposure time. The concentration of the molecular solution is expected to ultimately influence construct stiffness. The starting concentration will be studied at 1, 2, and 5 mg/mL of collagen. The collagen type is critical to the osteochondral construct. Both type I and type II collagen are found in bone and cartilage, respectively, and can be investigated at aforementioned concentrations.

Incorporation of mineral, proteoglycan, and crosslinking is expected to enhance the zonal differences and improve the mechanical integrity of collagen gels. Mineral content (e.g. hydroxyapatite incorporation at 1, 5 and 10 mg/mL) can be included directly (FIG. 2). Aggrecan and/or chondroitin/dermatan sulfate can be incorporated at graded concentration levels (0.3, 0.6, and 1.7 mg/mL; Sigma), considering the collagen concentrations and that proteoglycans amount for about 33% of the dry weight of cartilage. Genipin concentrations of 0.1, 0.5, and 1.0% can be studied to improve gel stiffness over at least 14 days of culture. Importantly, the incorporation of mineral, proteoglycan and crosslinking can maybe studied in a factorial design where all combinations will be considered for fine-tuning mechanical function.

Figure 3:
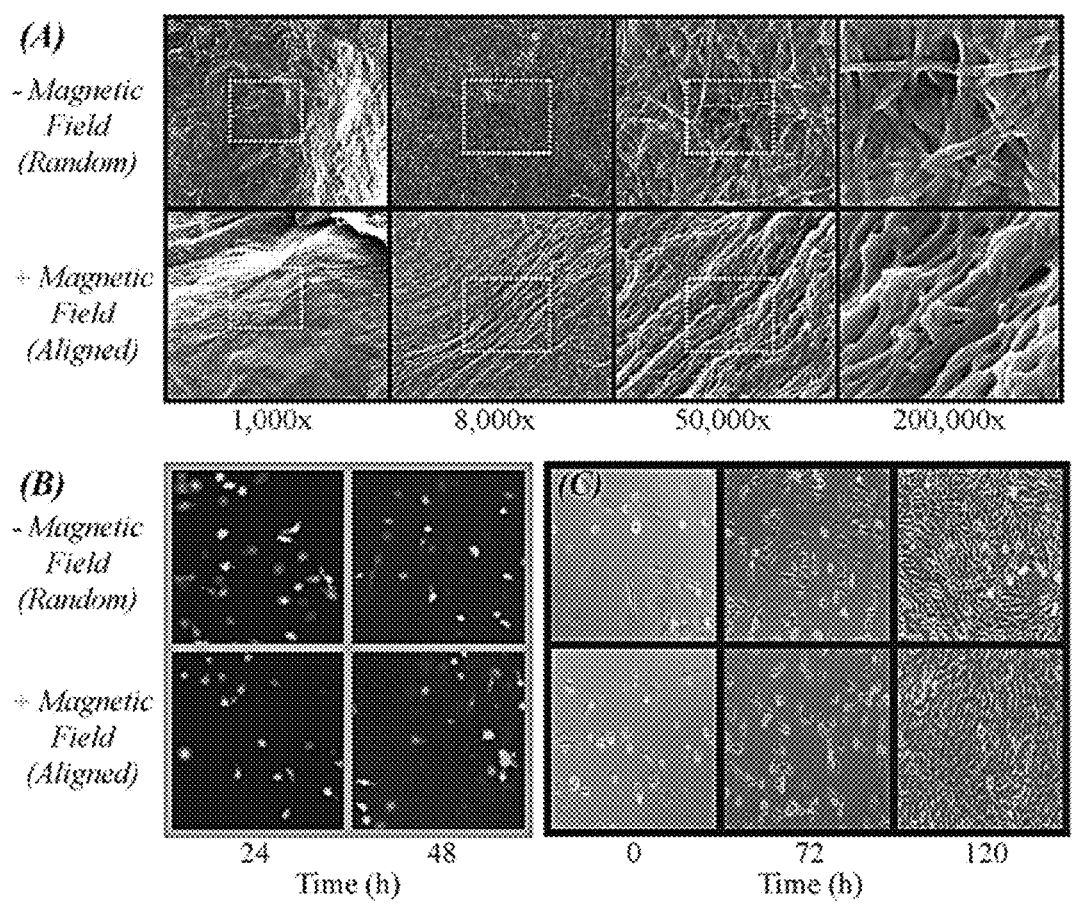
FIG. 3 depicts a series of images of collagen alignment using a superconducting high-field strength magnet (a) and depicts images of response of primary and progenitor cells to a superconducting magnetic using incorporation and viability (Live/Dead), and proliferation (cell count) assays, according to exemplary embodiments of the present disclosure.

Fiber alignment can be verified using birefringence and SEM measurements (FIGS. 2 and 3). Collagen gels can be placed under a polarized light microscope. The three orientation patterns in the gel can be examined by looking at the interface of the aligned gel using the polarized light microscope. Collagen alignment can be estimated by polarized light microscopy and parallelism. Additionally, SEM samples can be prepared using a freeze fracture technique. Images of the aligned gel can be compared against controls (randomly aligned-collagen gels) prepared using the same protocol as described above without the magnetic field exposure. Mechanical stiffness can be studied as described further below.

The functional lifespan post-implantation in vivo of MAP3D may depend on the incorporation of cells. Primary and progenitor cell populations can be studied. Primary chondrocytes can be extracted from the articular cartilage of young bovine knee joints (approximate age of 3 months) (FIG. 3). A custom cutting jig can be used to isolate zonal chondrocytes. Cells may be released by enzymatic digestion with 0.2% collagenase-P for 5 hours. During harvest, tissues and cells can be maintained chemically defined medium (DMEM/F-12) with supplements. If necessary, cells can be expanded in monolayer cultures (37° C., 5% $CO_2$). Bone marrow derived-progenitor cells can be purchased commercially (e.g. Thermo) or harvested from animals and cultured following recommended protocols. In the latter, calf forelimbs can be dissected under sterile conditions and plugs of humeral head cancellous bone marrow (0.5-1.5 mL) can be transferred to sterile tubes, containing BGJb medium (GIBCO) and 10% FBS. The tubes can be vortexed to disperse the marrow cells and centrifuged for 5 min at 1000 rpm. Marrow cells can be separated into a single cell suspension by passage through syringes and centrifuged to remove the fat layer and supernatant. Cells can be reconstituted in complete medium and plated in 100-mm dishes for expansion, if needed. According to an alternative embodiment, the process according to the disclosure can be configured to implant the cell-free scaffold in a full thickness defect and allow the patient's own progenitor cells from underlying bone marrow to infiltrate and populate the scaffold.

The use of primary and progenitor cells can be studied in separate constructs. Cells can be included in collagen solutions during magnetic alignment of each layer in varying cell densities (1, 5, and $10 \times 10^6$ cells/mL) from harvested populations to resemble native cartilage. Culture time is important to allow cellular protein expression to influence the local microenvironment. Cell culture time can be studied at 14, 28, and 56 days. If needed, mechanical compressive loading can be applied if it is found that cell death occurs especially in the center of fabricated constructs.

Figure 4:
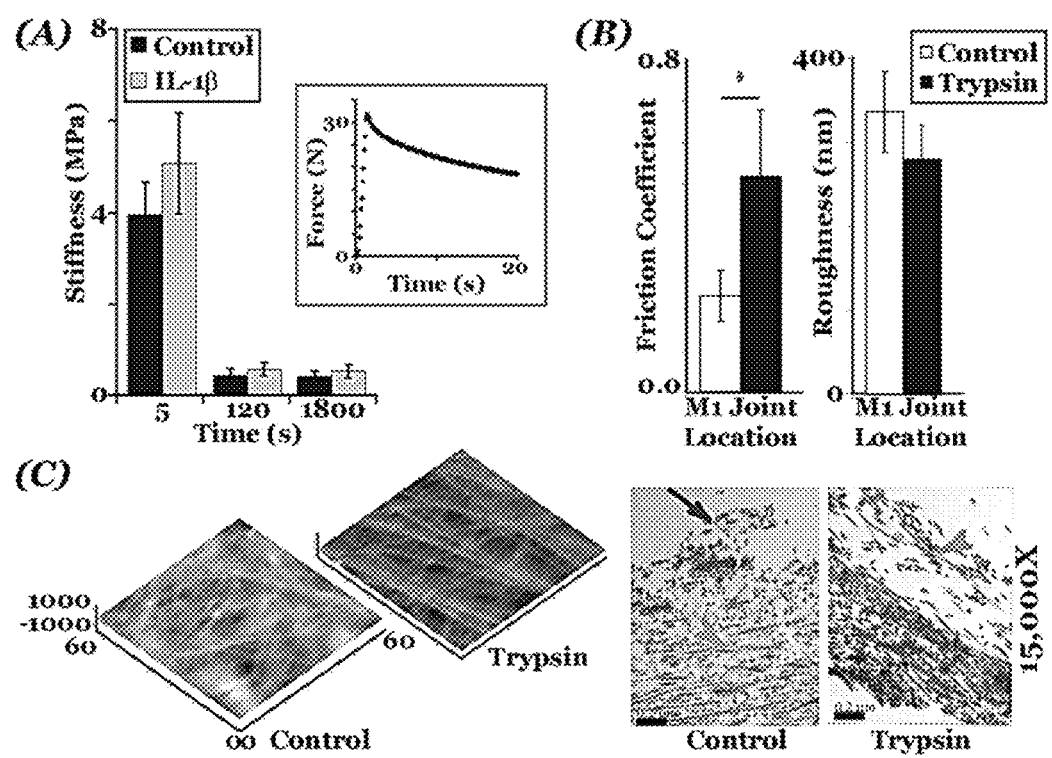
FIG. 4 depicts a plot of Stiffness in (MPa) vs. time obtained by stress relaxation experiments, a plot of friction coefficient vs. location MAP3D constructs according to the present disclosure, and images of the MAP3D constructs, according to exemplary embodiments of the present disclosure.
Figure 5:
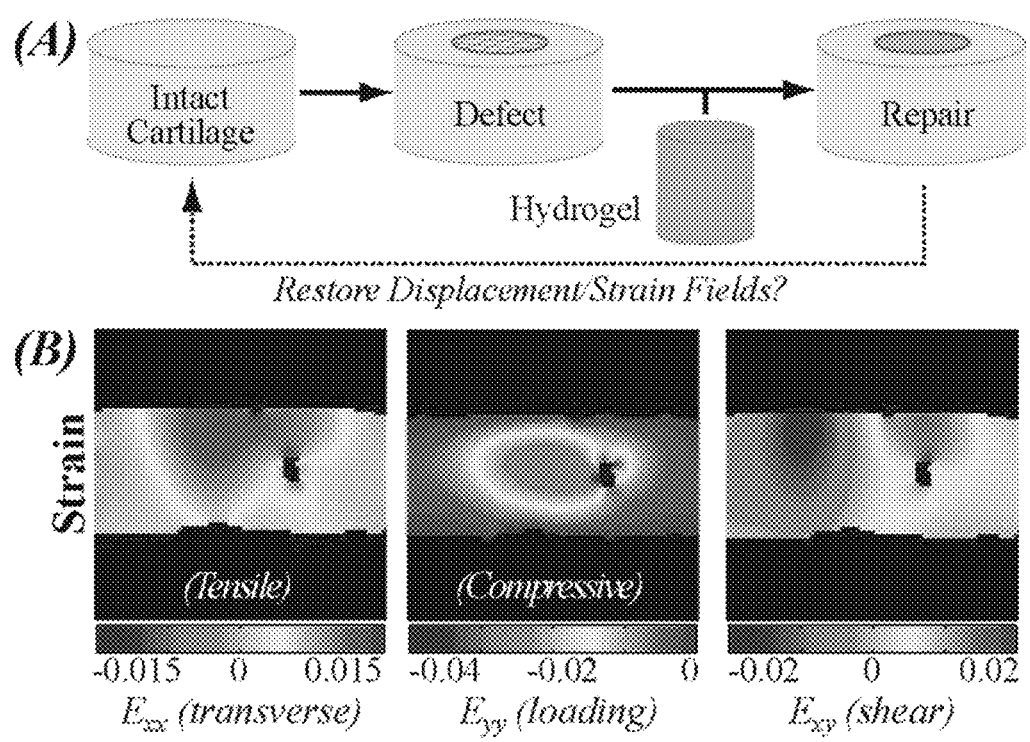
FIG. 5 depicts a schematic of an MRI-based strain analysis procedure, and MRI-based strain image, according to exemplary embodiments of the present disclosure s.

Samples can undergo surface, bulk, and depth-dependent mechanical characterization by AFM, unconfined compression, and MRI, respectively (e.g. FIGS. 4 and 5). Friction can be assessed at the macroscale using a pin-on-disk tribometer and at the nanoscale by AFM in the contact mode while immersed in PBS to maintain tissue hydration. Unconfined compression can determine intrinsic tissue mechanical properties. Depth-dependent strain patterns under cyclic compressive loading can be determined by displacement-encoded MRI. Strain patterns can be determined using phase contrast data converted to zonal strain distributions.

Animal experiments can be performed under IACUC-approved protocols. Engineered constructs can be implanted into multiple osteochondral defects created in the medial condyle of the distal femur of the right knee. Both the lateral condyle and left knee can be left untreated for comparison. In one example, a total of 14 skeletally-mature female adult sheep (weight≈70 kg; age≈3-4 years) can be enrolled in this study. The total of 14 animals was derived from 12 animals (6 animals per group (i.e. n=6; described subsequently)×2 time points) plus an additional 2 animals used as a cell source for MAP3D repair tissue. The use of larger animals allows for a nested analysis; multiple defects may be created in each animal in tissue regions that may be expected to undergo similar mechanical loading in vivo. The number of samples (n=6) was determined using a power analysis based on $(\mu_1/\sigma)=2.8$, a conservative estimate in which a difference in the means of 9 was observed for histochemical scoring between defect treatments with a (largest observed) standard deviation of about 3. Thus, n=6 can protect against potential experimental problems and provide a sufficient sample size.

Surgery can be conducted under general anesthesia and sterile conditions. Knee joints may be opened with a ventomedial arthrotomy along with careful lateral subluxation of the patella. Osteochondral defects (5 mm diameter; 5 mm depth) can be developed using a trephine from the central weight-bearing region and appropriately spaced to minimize interactions of treatment effects at each location and maintain joint stability. The defects can be managed using one of five treatments: the removed osteochondral fragments can be placed back in the defect (group I; positivecontrol); the defect can be left empty (group II; negative control); layered constructs (Aim 1; group III), and cellularized and layered constructs (Aim 2; group IV) can be placed in the defect. Following surgery, the patella can be put back in place and checked for proper patellar tracking. The joint can be closed in layers. The sheep can be allowed to move freely immediately following recovery from anesthesia. Animals may then be sacrificed with an overdose of sodium pentobarbital at 3 and 24 weeks after the operation to evaluate the repair time course.

Figure 6:
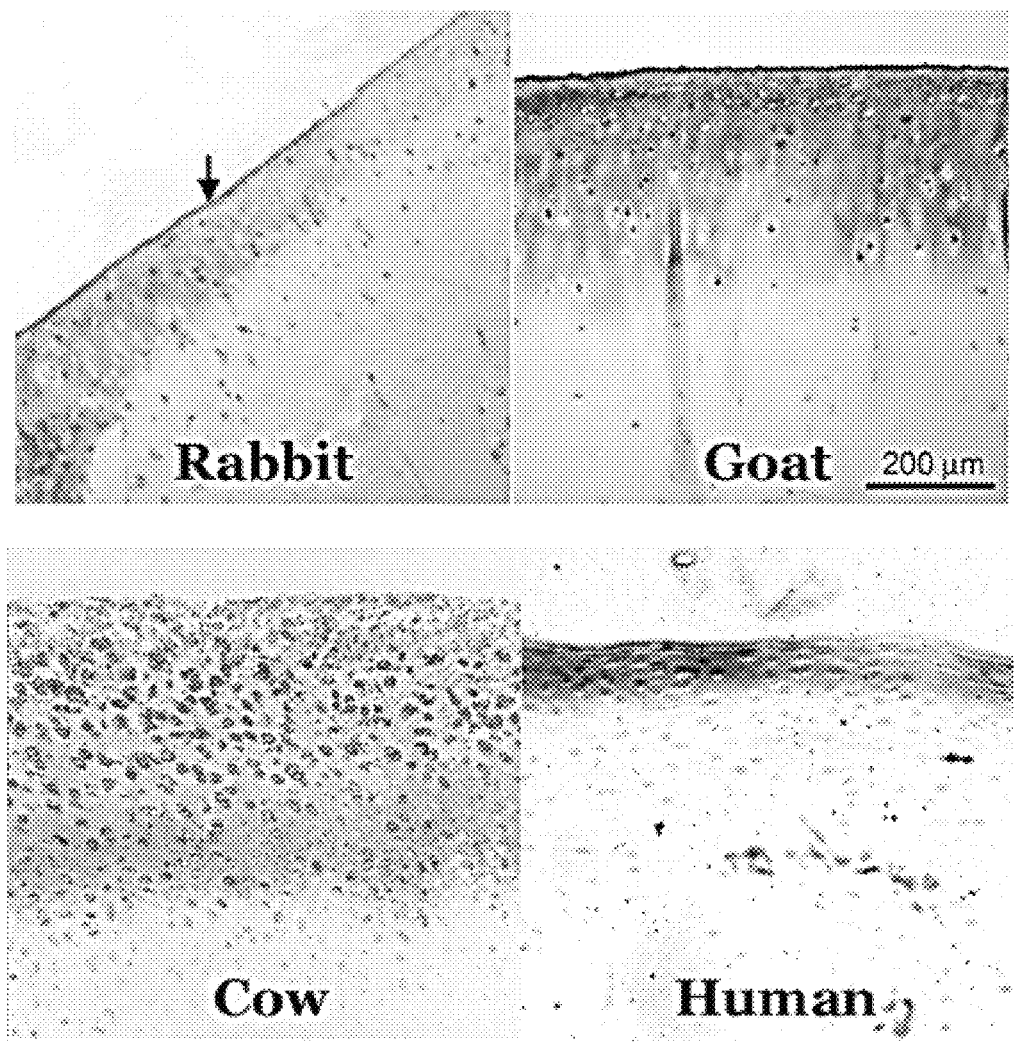
FIG. 6 depicts schematic images of osteochondral proteins (e.g. superficial zone protein) that can be localized in MAP3D repairs using specialized antibodies (e.g. S6.79 for SZP).

The success of osteochondral defect repairs for sheep can then be evaluated by mechanical testing (as described above) and histochemistry. Standardized scoring systems can reveal gross morphology and lateral tissue integration following staining by hematoxylin and eosin (H&E) and Safranin O. Distribution of key zonal osteochondral proteins can be evaluated with specialized antibodies, see FIG. 6 (e.g. superficial zone protein (SZP)). Images can be obtained with an optical microscope at 100× magnification.

Example 1

The disclosure of the present application also includes disclosure that fibrillogenesis (fibril assembly) and alignment could be extended at low temperatures to create controlled alignment profiles through the interior of collagen scaffolds. One objective was to manipulate the collagen fibrillogenesis time through temperature control to achieve high degrees of alignment while maintaining the physiological pH.

For this study, Type I oligomeric collagen was extracted from porcine dermis to a concentration of 5.6 mg/mL. Collagen was then neutralized to a final concentration of 3.2 mg/mL using 10×PBS and 0.1N NaOH. Control (random) scaffold collagen solutions, prepared without the use of magnetic field alignment, were polymerized at various temperatures between 15° C. and 37° C. in an incubator (MIR-154, Sanyo). Aligned scaffolds were polymerized within a 9.4 Tesla vertical-bore superconducting magnet (CMX 400, Chemagnetics) at either 18° C. or 37° C. for the present fibril orientation studies. Scaffolds were formed inside plastic chambers, approximately 10×10×5 mm, bound by No. 1 confocal coverslips (VWR) to facilitate imaging. Fibrillogenesis time was assessed using turbidity data. For turbidity of control scaffolds, spectrophotometric data was acquired at 30 second intervals using a 313 nm wavelength light source (n=3 for each group). Temperature control was achieved through the use of a refrigerated water-pump (Isotemp 3006D, Fisher Scientific) and verified by an external thermocouple.

Collagen scaffolds were analyzed using polarized light (bulk) and confocal reflection (microscale) microscopy. For polarized light microscopy (PLM), a full wavelength retardation plate was used to distinguish a red-blue color shift in aligned scaffolds. Scaffolds (n=12) were placed on a rotating stage and imaged at 5° intervals through a 180° arc using a Leica DFC480 CCD camera. A micrometer was used to shift the field of view and acquire alignment data through the depth of the scaffold. The parallelism index (PI) was determined as previously described. For confocal reflection microscopy, microscale fibril alignment was assessed by an Olympus Fluoview FV1000 microscope system (488 nm) with a 40× water immersion objective. An image volume (zstack; 5 images with a 50 µm interslice distance) was performed at up to nine separate locations within each scaffold (n=12). Fiber alignment was assessed using a custom two-dimensional Fast Fourier Transform (FFT) based algorithm (MATLAB). Image intensity of the FFT results was radially summed to determine preferred alignment angles. Angle alignment with a range of up to 70 degree variation with respect to desired point of alignment on an axis (reference point), for example, may be used in connection with various embodiments. The aspect ratio of a best-fit (linear) ellipse was determined from long and short axes, representing the degree of alignment.

Confocal and turbidity data were analyzed using SAS/STAT® software. Aspect ratios were compared using a mixed-model ANOVA with samples as a random effect. Magnetic field, temperature, z-stack, and depth into scaffolds were treated as fixed main effects. All fixed effect interactions were included. Fibrillogenesis times were compared using a one-way ANOVA and temperature as a fixed main effect.

Figure 7:
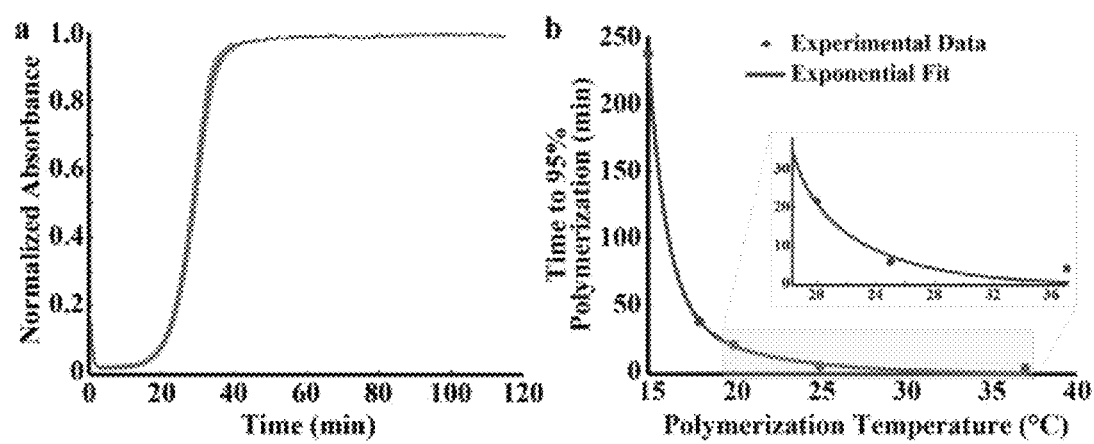
FIG. 7 depicts a representative turbidity profile (sub(a)) and fibrillogenesis times (sub(b)) expressed as a time to reach 95% maximum absorbance following a two-parameter exponential decay with increasing temperatures, according to exemplary embodiments of the present disclosure.
Figure 8:
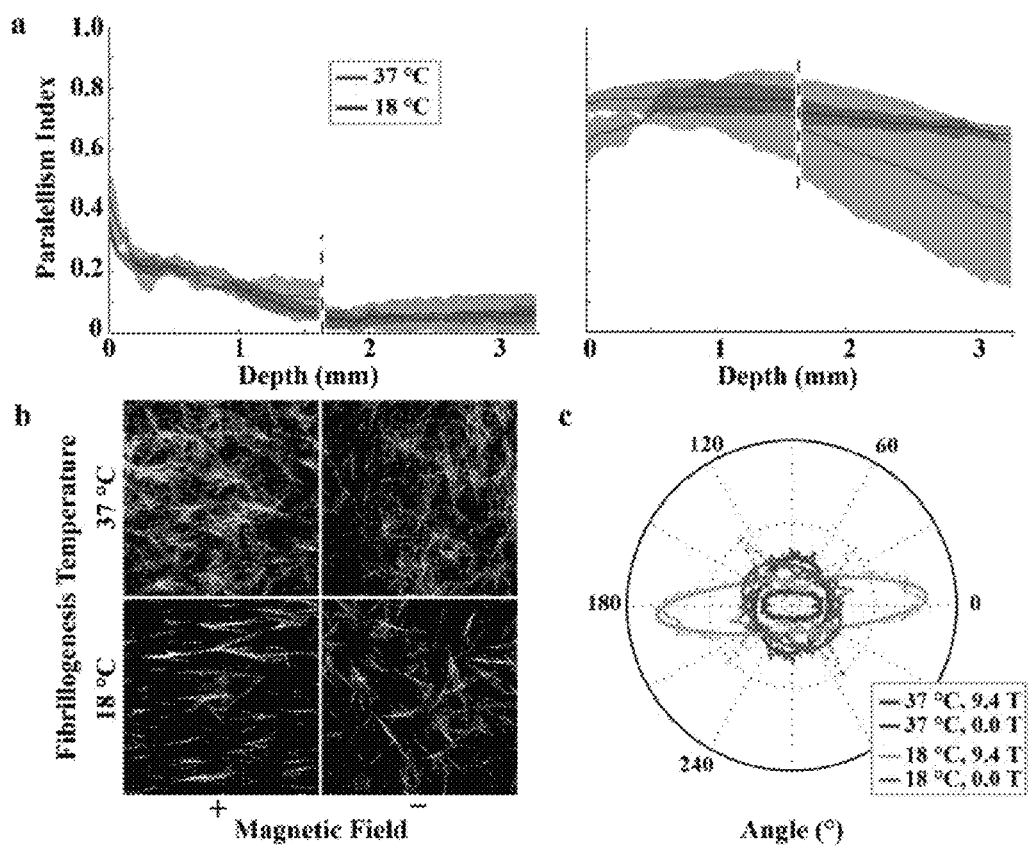
FIG. 8 depicts parallelism index (PI) curves without (sub(a)) and with (sub(b)) magnetic alignment, along with microscope images at two temperatures with and without alignment (sub(c)) with a corresponding polar plot (sub(d)), according to exemplary embodiments of the present disclosure.

Results: Full thickness collagen alignment was successfully demonstrated using temperature-controlled fibrillogenesis. Collagen scaffolds were successfully created and imaged at varying temperatures (18° C. and 37° C.). Turbidity data showed an inverse relationship between temperature and fibrillogenesis time ($p<0.0001$), as shown in FIG. 7. As shown in FIG. 7, (a) is a representative (sigmoidal) turbidity profile generated at 18° C., and (b) shows fibrillogenesis times expressed as time to reach 95% maximum absorbance following a two-parameter exponential decay with increasing temperatures ($R2=0.9969$). Under crossed polarizers, collagen scaffolds formed absent of a magnetic field appeared similar at differing temperatures, whereas scaffolds formed within a 9.4 T magnetic field show a depth-dependent PI influenced by temperature, as shown in sub(a) of FIG. 8. As shown in FIG. 8, the parallelism index (PI) indicates control (random; 0 T) (a) and bulk (9.4 T) alignment (b) in collagen following 18° C. and 37° C. exposure. Within the first chart shown in sub(a) of FIG. 8, the relatively lighter (37° C.) sample starts out with a higher PI, dips below the 18° C. sample before 0.5 mm depth, approaches the 18° C. sample around 0.5 mm, and extends above the 18° C. sample around 1.5 mm depth. The 18° C. sample generally decreases from 0 to around 2 mm depth. In the second chart shown in sub(a) of FIG. 8, the darker and relatively narrower portion is the 18° C. sample, while the lighter and much broader sample between 2-3 mm, for example is the 37° C. sample. Samples formed at lower temperatures maintain alignment throughout the depth of the scaffold, indicating more consistent alignment throughout the scaffold volume. The gap (dashed line) represents the acquisition of two adjacent fields of view. Sub(b) of FIG. 8 shows qualitative differences between 18° C. and 37° C. magnetic alignment can be seen by confocal microscopy. Although the magnitude of the PI was consistent between temperatures, confocal data demonstrated that lower temperatures promoted a more aligned microstructure in a 9.4 T magnetic field ($p=0.010$), as shown in sub(b) and sub(c) of FIG. 8. Data revealed nonhomogenous alignment throughout the scaffold thickness ($p=0.0029$). Further, sub(c) shows polar plots of FFT magnitude reveal preferred fibril distributions. Within sub(c) of FIG. 8, the outermost ring (widest oval) represents 18° C., 9.4 T, the next inner ring is 18° C. at 0 T, the next ring (similar in size to the 18° C. 0 T ring, but shown more vertically) is 37° C. at 0 T, and the innermost ring is 37° C. at 9.4 T. Collagen gels formed at 18° C. at 9.4 T exhibit much higher alignment, as shown by FFT-derived elliptical aspect ratios.

As noted above, the present disclosure includes disclosure of the use of temperature as a tunable parameter for obtaining targeted degrees of fibril alignment for collagen scaffolds formed within a magnetic field. Superior alignment achieved through other methods such as electrospinning is a primary deterrent to magnetic alignment techniques; however, scaffold formation at lower temperatures offers increased alignment potentially making this a more attractive option for biomimetic scaffold development for the treatment of osteoarthritis, for example. Temperature control also influenced the volume of the scaffold that appears aligned. While scaffolds formed at 37° C. showed alignment only in the center, with decreasing PI throughout the scaffold thickness, collagen formed at 18° C. showed alignment throughout the full width and thickness of the scaffold. Images acquired under PLM confirmed the temperature-dependent spatial variation in alignment throughout full thickness scaffolds. These data indicate that temperature control during fibrillogenesis could serve to modulate the spatial variation in alignment, for example.

Example 2

To better mimic the articular cartilage ultrastructure, the present disclosure includes disclosure of using oligomeric collagen, with inherently higher mechanical properties compared to commercially available monomeric forms, in addition to nondestructive magnetic alignment of collagen fibrils and incorporation of glycosaminoglycans (GAGs), for example. In the present example, novel collagens, alignment methods, and matrix augmentation were combined to improve scaffold mechanical properties toward those observed in articular cartilage. One aim was to measure mechanical properties for combinations of oligomeric collagen, magnetic alignment, GAG incorporation, and the use of exogenous cross linkers. An additional aim was to measure mechanical properties in layered scaffolds approaching the zonal ultrastructure of cartilage.

For the present example, type I oligomeric collagen was purified from porcine dermis and solubilized at a concentration of 7.5 mg/mL. Collagen solutions (n=5) were neutralized and polymerized in glass cylinders (inner diameter=10 mm, height=7.5±0.5 mm). Scaffolds were magnetically aligned and polymerized in a 9.4 Tesla (T) vertical bore superconducting magnet (CMX400, Chemagnetics) at controlled 18° C. (2 hour) and 37° C. (1 hour) temperatures. Control (unaligned) scaffolds were polymerized using the same method, but in absence of the magnetic field. Layered constructs were fabricated using successive polymerization with and without the presence of the 9.4 T field as required by the sample. Fibril alignment was confirmed by polarized light (data not shown) and confocal microscopy.

In order to emulate the biological and physical properties of articular cartilage, glycosaminoglycan and crosslinking treatments were applied pre- and post-polymerization, respectively. Hyaluronic acid (CALBIOCHEM) was mixed into the neutralized solution at 10 mg/mL. Post-polymerization crosslinking of scaffolds was performed through EDAC/NHS (Sigma) crosslinking at a 5:2:1 EDAC:NHS:COOH molar ratio.

Collagen scaffolds were tested in unconfined compression using aservoelectric materials testing system (TestResources). The scaffolds were compressed in 5% nominal strain increments at a strain rate of 17.9% sec-1 coupled with a 25 sec hold (stress relaxation) period. Engineering stress was determined using initial sample geometry and a 1000 g load cell (LPM 512, Cooper Instruments) at a sampling rate of 100.

Figure 9:
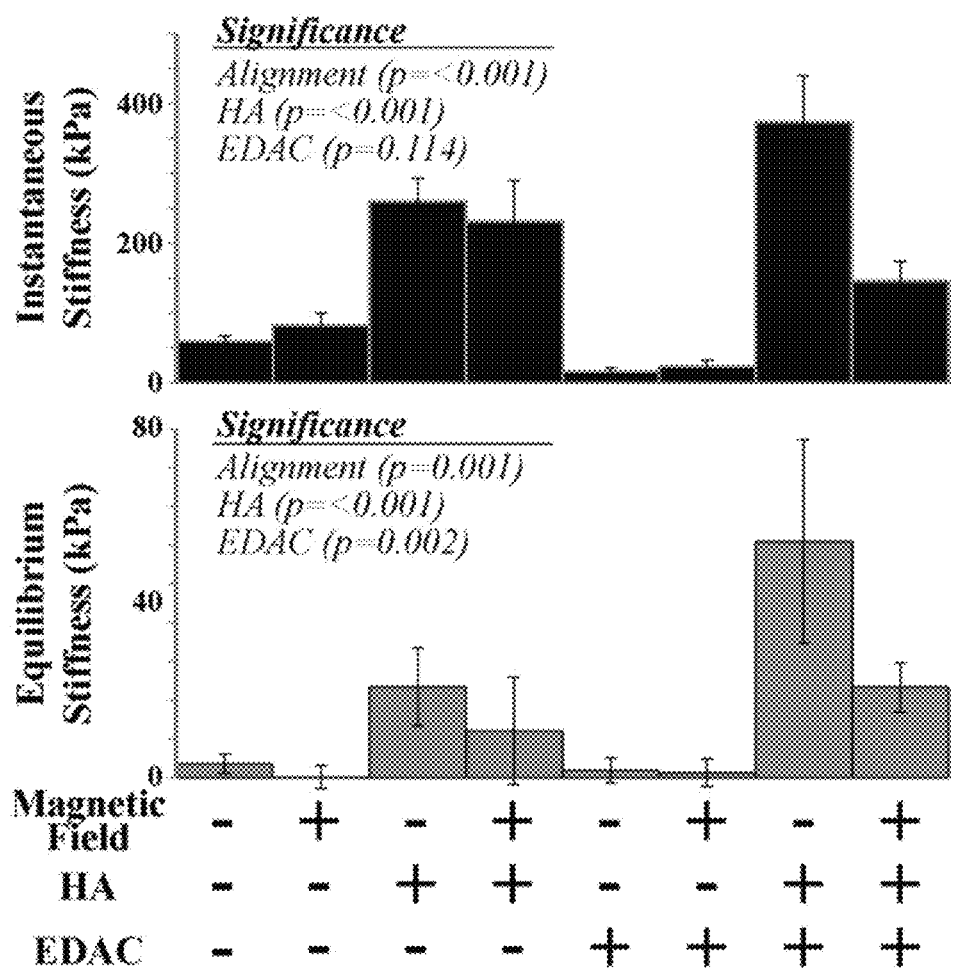
FIG. 9 depicts instantaneous stiffness and equilibrium stiffness charts for various collagen constructs, with and without magnetic field, hyaluronic acid, and EDAC crosslinking, according to exemplary embodiments of the present disclosure.

Results: The stiffness measures for collagen constructs varied by treatment, as shown in FIG. 9. As shown therein, oligomeric collagen can be mechanically augmented via magnetic alignment, hyaluronic acid incorporation, and EDAC crosslinking. Both instantaneous and equilibrium stiffness are affected by pre- and post-polymerization augmentations to collagen scaffolds. Magnetic alignment of collagen significantly increased the instantaneous stiffness ($p=<0.001$) and decreased the equilibrium stiffness ($p=0.001$). Hyaluronic acid incorporation increased both the instantaneous ($p=<0.001$) and equilibrium ($p=0.001$) stiffness. EDAC crosslinking increased the equilibrium ($p=0.002$), but not instantaneous ($p=0.114$), stiffness. All instantaneous stiffness interactions were significant ($p<0.007$), as were all equilibrium stiffness interactions except MA/EDAC ($p=0.111$) and MA/HA/EDAC ($p=0.053$).

Figure 10:
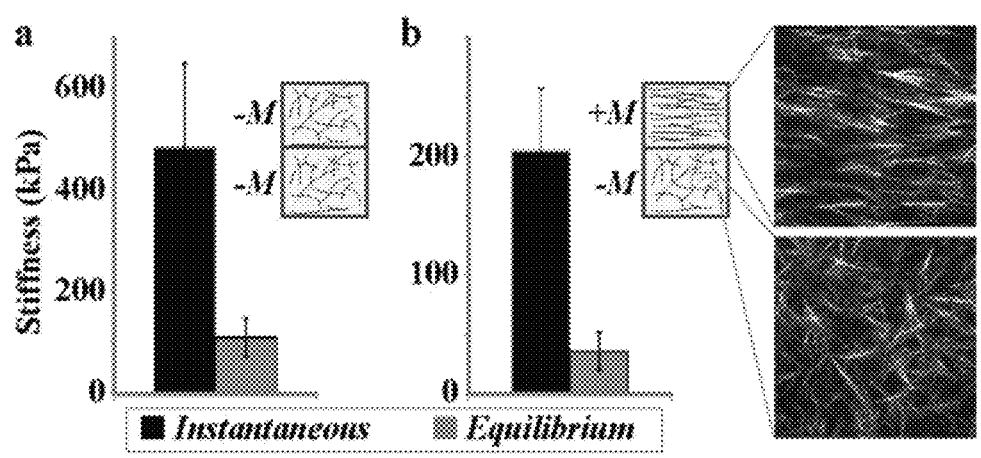
FIG. 10 depicts instantaneous (sub(a)) and equilibrium (sub(b)) stiffness charts for unaligned and aligned samples, according to exemplary embodiments of the present disclosure.

Layered scaffolds were mechanically similar to single layer scaffolds for both unaligned and aligned scaffolds, as shown in FIG. 10. As shown therein, layered scaffolds create complex, depth-dependent materials that begin to emulate the native structure of cartilage. Layering of scaffolds yielded mechanical properties similar to the single layer properties, suggesting the bulk of the deformation occurred in the top layer near the load application for unaligned (a) (−M/−M) and aligned/unaligned (b) (+M/−M) scaffolds. Confocal microscopy confirmed alignment of collagen scaffolds. An aligned top layer significantly decreased the instantaneous ($p=0.023$) and equilibrium stiffness ($p=0.009$).

As shown in the aforementioned figures and referenced above, the combinatorial use of oligomeric collagen, magnetic alignment, glycosaminoglycan incorporation, and exogenous crosslinking was shown to better mimic the mechanical, architectural, and physicochemical properties of collagen scaffolds. The equilibrium compressive properties of aligned and unaligned scaffold treated with HA and EDAC begin to approach physiological mechanical properties, where native articular cartilage has equilibrium stiffness ranging from 0.31-0.8 MPa. This is in contrast to other current collagen technologies which are able to reach an instantaneous compressive stiffness ≤77 kPa and an equilibrium compressive stiffness of ~1 kPa after exogenous crosslinking. Much of the mechanical viability of the constructs must be attributed to the use of oligomeric collagen, which has inherently high mechanical properties and which is constructed of a more matured collagen network, more similar to the native physiology. The magnetic alignment of the oligomeric collagen allows for a small degree of mechanical tuning and provides a nondestructive method for aligning collagen fibrils. HA inclusion allows for tissue-level mechanical properties and mimics the biochemical properties of healthy articular cartilage. EDAC crosslinking adds an additional level of control over mechanical properties. This study provides a foundation for the manipulation and control of mechanical, architectural, and physicochemical properties, to better mimic collagen-rich tissues like articular cartilage.

The development of a layered scaffold with an aligned top layer and a random bottom layer, for example, shows the potential to replicate the depth dependent fibril structure of articular cartilage. During these tests, it was observed that the impacted (top) layer of the scaffold experienced greater compressive stain than the bottom layer. This is the mechanism of action for the decrease in mechanical properties, as it is consistent with the effect of HA and magnetic alignment in single layer tests.

Example 3

In this example, two temperatures (18° C. and 37° C.) were used in connection with aligned and non-aligned (control) collagen-based products, with alignment using MAP3D technology that does not require a high voltage potential or electrochemical interactions while avoiding the possibility of collagen denaturing.

Figure 11:
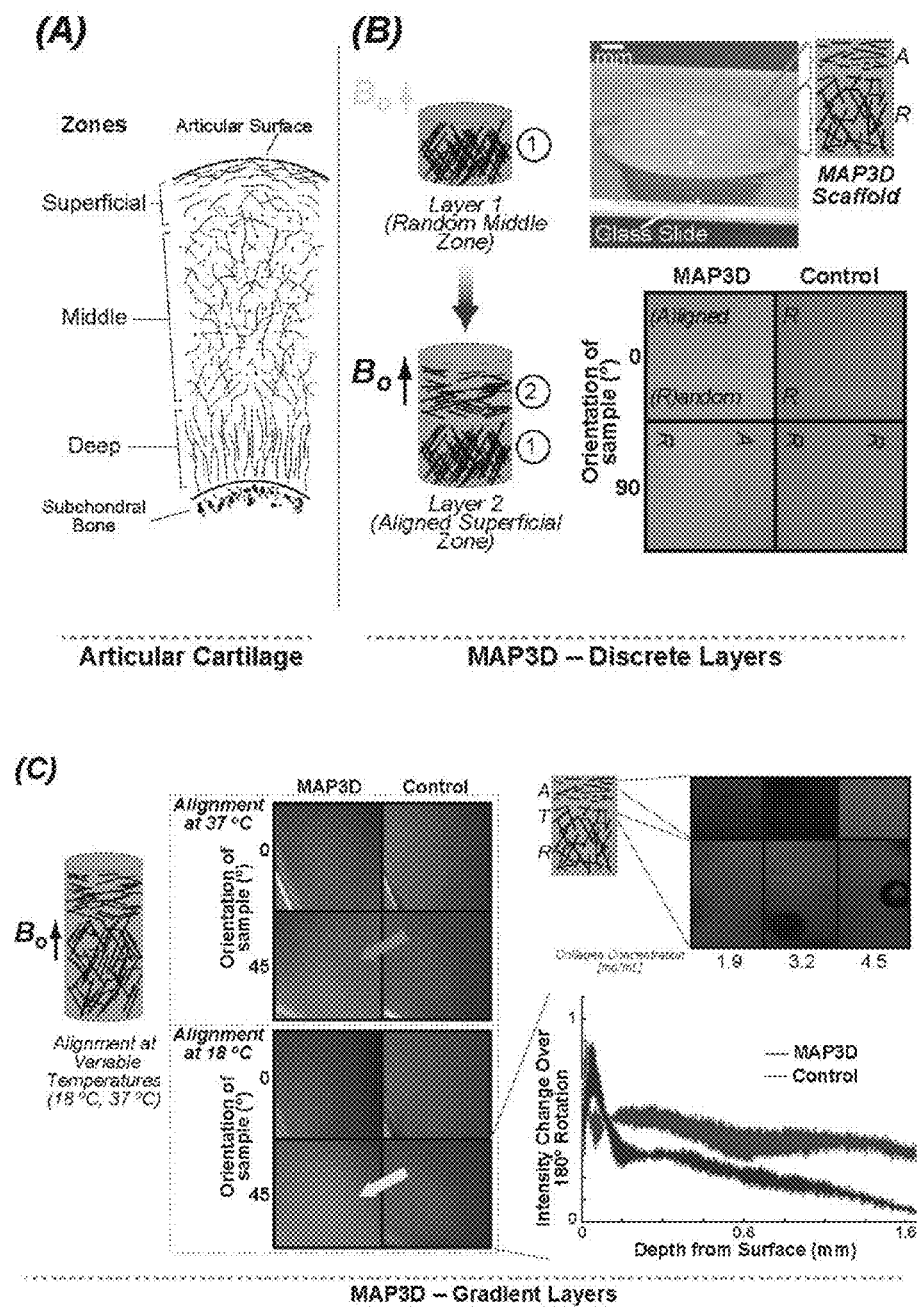
FIG. 11 depicts various regions of articular cartilage (sub(A)), discrete layers made using MAP3D (sub(B)), and the use of temperature to control the thickness of alignment (sub(C)), according to exemplary embodiments of the present disclosure.

FIG. 11 shows several depictions relating to the foregoing, using MAP3D technology that mimics the articular cartilage ultrastructure through the fabrication of stratified (zonal) and aligned collagen scaffolds with discrete or gradient layers. Sub(A) of FIG. 11 shows various regions of articular cartilage, extending from subchondral bone at the deep layer, to the middle layer, and finally to the superficial layer ending at the articular surface. Sub(B) of FIG. 11 shows discrete layers of collagen resulting from a step-wise fibrillogenesis with and without an external magnetic field ($B_o$) to create to aligned structures. Polarized microscopy confirms the expected birefringence in the aligned compared to random layers. Sub(C) shows that gradient layers result in the presence of $B_o$ and variable temperature to control the thickness of alignment, with a smooth transition (T) from the aligned (A) to random (R) zone. MAP3D fabrication at 37° C. for one hour results in partial alignment and a transition zone (upper arrow), while fabrication at 18° C. for 12 hours results in a full-thickness aligned scaffold (lower arrow). Alignment is confirmed by intensity changes, and birefringence depends on collagen concentration (insets). Importantly, other biomolecules (e.g. proteoglycans) and cell populations may be added during MAP3D fabrication. Within the portion of sub(c) of FIG. 11 depicting intensity change over 180° rotation, the upper curve at 0.8 mm, for example, represents MAP3D, while the lower curve at 0.8 mm represents the control.

Use of this highly versatile technology can control zonal collagen alignment, with discrete or gradient layers, in the absence of any degrading interaction with the fibrils. MAP3D can utilize the additive diamagnetic properties of the peptide bond to torque fibrils into a state of alignment perpendicular to the applied magnetic field, as shown in FIG. 11. Since strain patterns in cartilage under mechanical loading are known to correlate with regions of fibril alignment, one aim is to monitor the bulk and regional mechanical properties of tissue scaffolds with zonal alignment similar to native cartilage. Altered mechanical properties due to zonal and gradient fibril alignment would be indicative of physiological similarity to cellular mechanical, biological, and structural microenvironments of articular cartilage. While osteoarthritis is a complex disease with a multifactorial (e.g. biomechanical and biochemical) etiology, MAP3D emulation of the physiological environment has potential to drive the infiltration, differentiation, and lubricating protein expression of chondrocytes.

Figure 12:
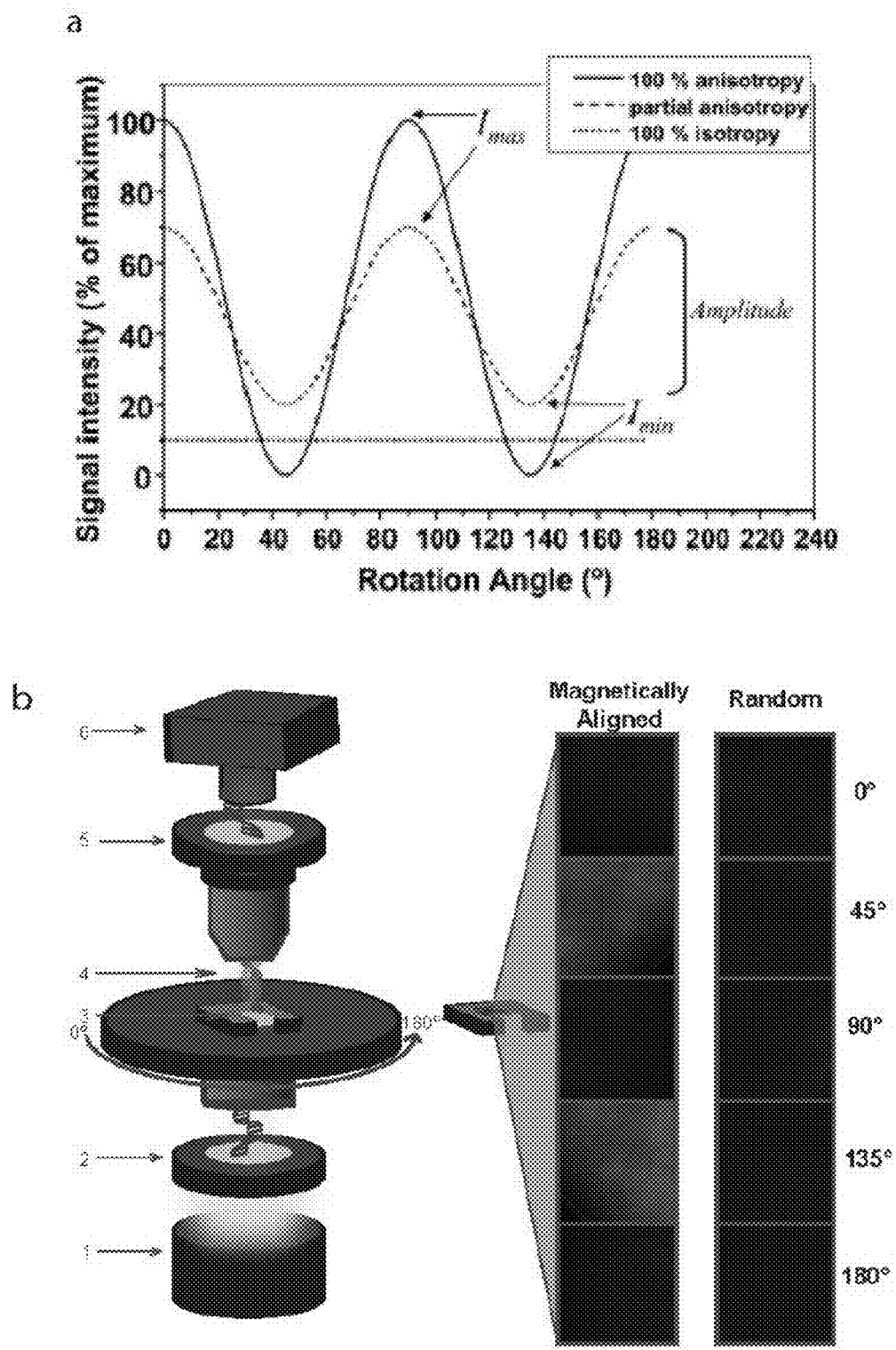
FIG. 12 depicts signal intensity versus rotation angle for full, partial, and no anisotropy (sub(a)) and components of an exemplary polarized light microscopy setup (sub(b)), according to exemplary embodiments of the present disclosure.
Figure 13:
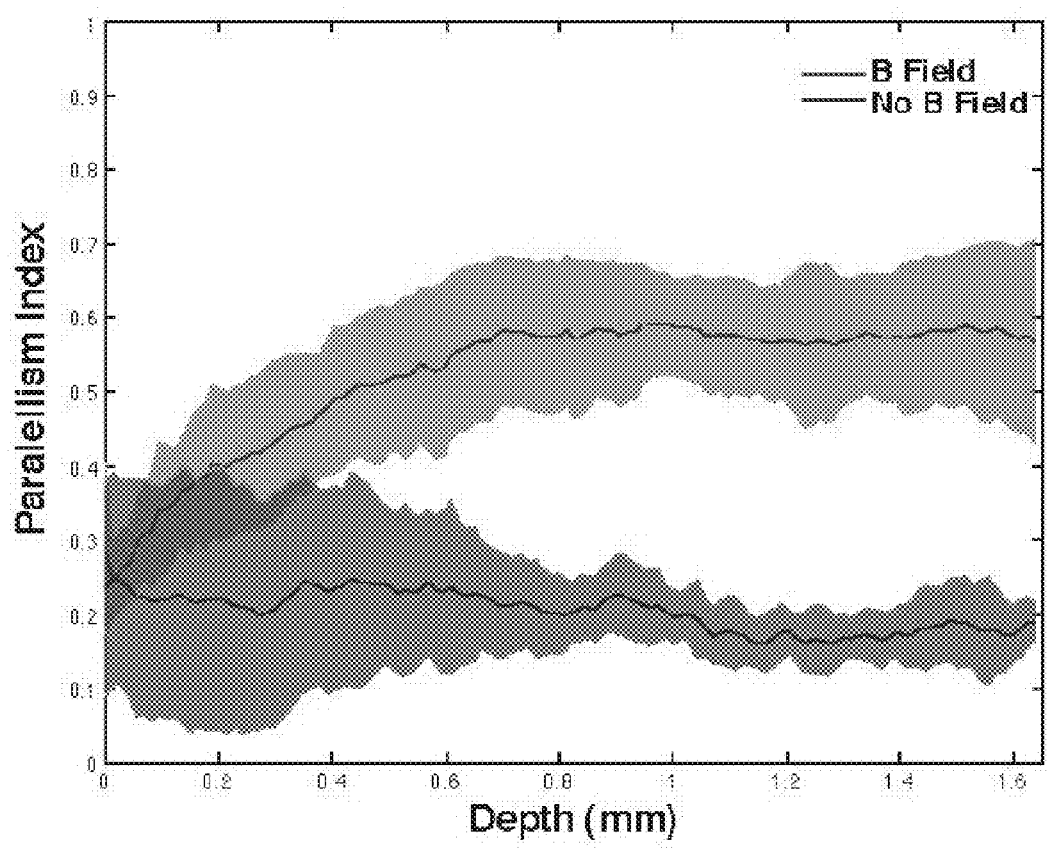
FIG. 13 depicts a parallelism index as a function of depth for aligned and unaligned samples, according to exemplary embodiments of the present disclosure.

Multiple assays were also established for collagen alignment anisotropy based on polarized and confocal microscopy. For polarized light microscopy (PLM, as shown in FIG. 12), a custom setup allowed for the noninvasive assessment of anisotropy by taking advantage of the natural birefringence of the collagen scaffold structure. With this imaging technique, bulk and regional alignment of the scaffolds was possible, with an imaging field of view covering hundreds of microns and containing thousands of individual collagen fibrils. Measurement of the signal intensity versus the rotation angle of the sample allows for the quantification of the parallelism index, which we found to depend on the depth of the scaffold when formed at 37° C., as shown in FIG. 13. FIG. 12 generally relates to the use of Polarized Light Microscopy (PLM) to quantify collagen alignment anisotropy. Sub(a) of FIG. 12 shows a sample sigmoidal curve of image intensity variation during sample rotation for various levels of anisotropy. Sub(b) shows an illustration of the polarized light microscopy setup, with (1) being a light source emitting nonpolarized light, (2) being a 0° polarizing filter, (3) being a collagen gel within silicon chamber secured by coverslips, (4) being linear, perpendicular polarized light waves emitting from birefringent (anisotropic) specimen, (5) being a 90° polarizing filter, and (6) being an exemplary suitable camera, such as a Leica DFC460 CCD camera (Leica Microsystems). Images from the polarized light microscope show varying intensity throughout the sample rotation. Aligned samples show high peaks when the fibers are oriented 45° to the crossed polarizers. FIG. 13 shows a Parallelism Index as a function of depth for aligned (upper) and unaligned (lower) samples.

Figure 14:
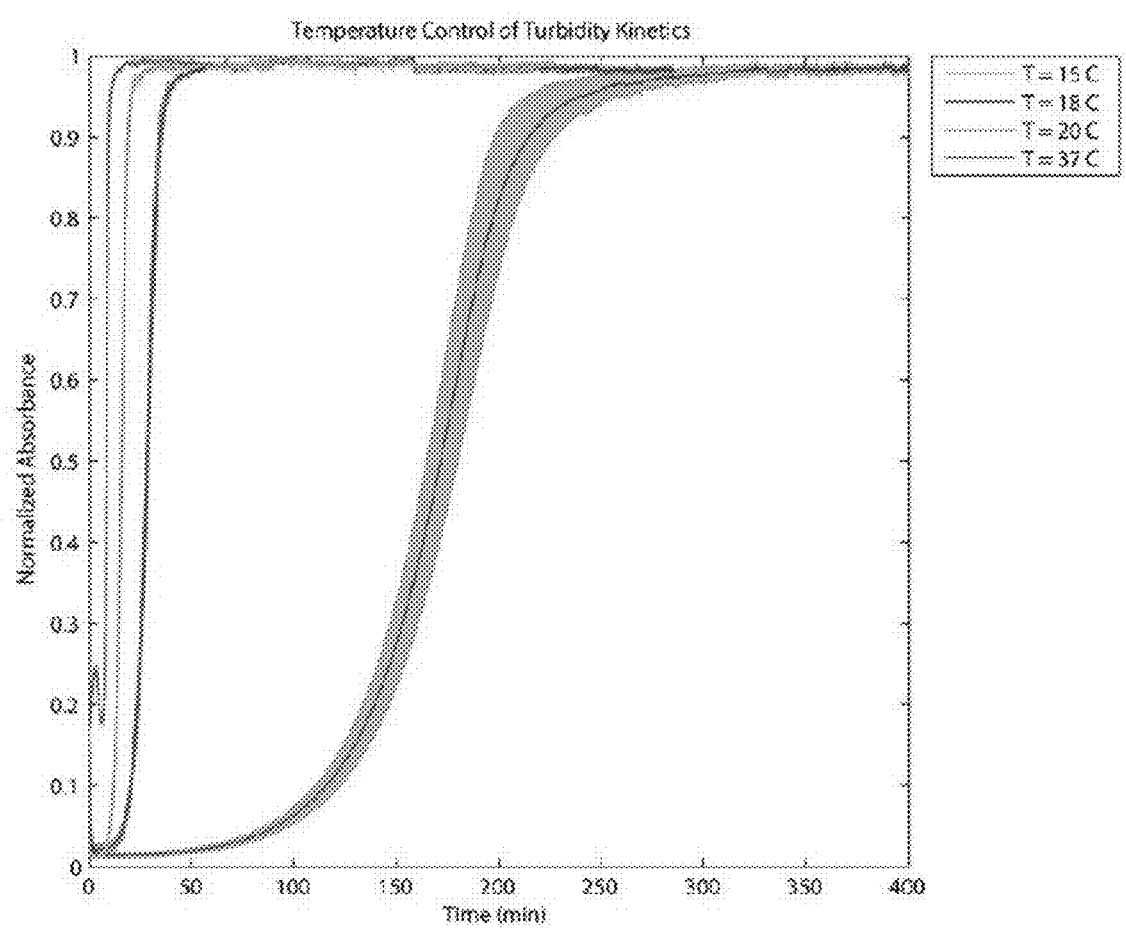
FIG. 14 depicts that turbidity kinetics can be manipulated by temperature control, according to an exemplary embodiment of the present disclosure.
Figure 15:
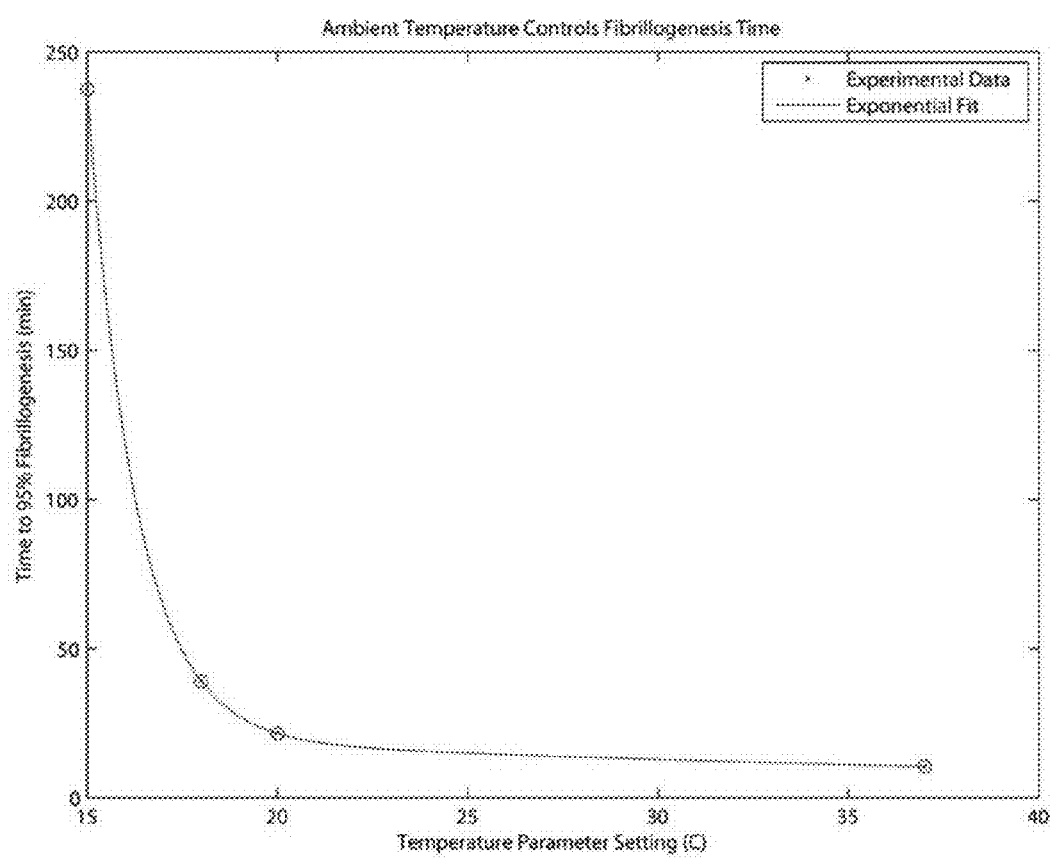
FIG. 15 depicts the time to reach 95% fibrillogenesis at different temperature settings, according to exemplary embodiments of the present disclosure.

Additional data relating to how temperature changes impact collagen alignment are shown in FIGS. 14, 15, 16, and 17. FIG. 14 shows that turbidity kinetics can be manipulated by temperature control. High temperatures initiate fibrillogenesis rapidly and polymerization occurs over very short time periods. Lowering of the ambient temperature slows down polymerization initiation as well as the time to reach maximum turbidity. Within the graph itself, the first line (initially most left) represents 15° C., the second line represents 18° C., the third line represents 20° C., and the fourth line (widest and most set apart from the other lines on the middle to right side of the figure) represents 37° C. FIG. 15 shows that the time to achieve 95% fibrillogenesis, as measured by absorbance, can be highly controlled through temperature manipulation. Fibrillogenesis time decreases exponentially as temperature is raised from 15° C. to 37° C. A fit equation consistent with FIG. 15 is:

$$\text{Time(in minutes)}=ae^{bx}+ce^{dx}$$

where a=0.6137, b=−7.735, c=16.04, d=−0.2888, and x is the temperature in Celsius; SSE=near 0, and R-square=1.

Figure 16:
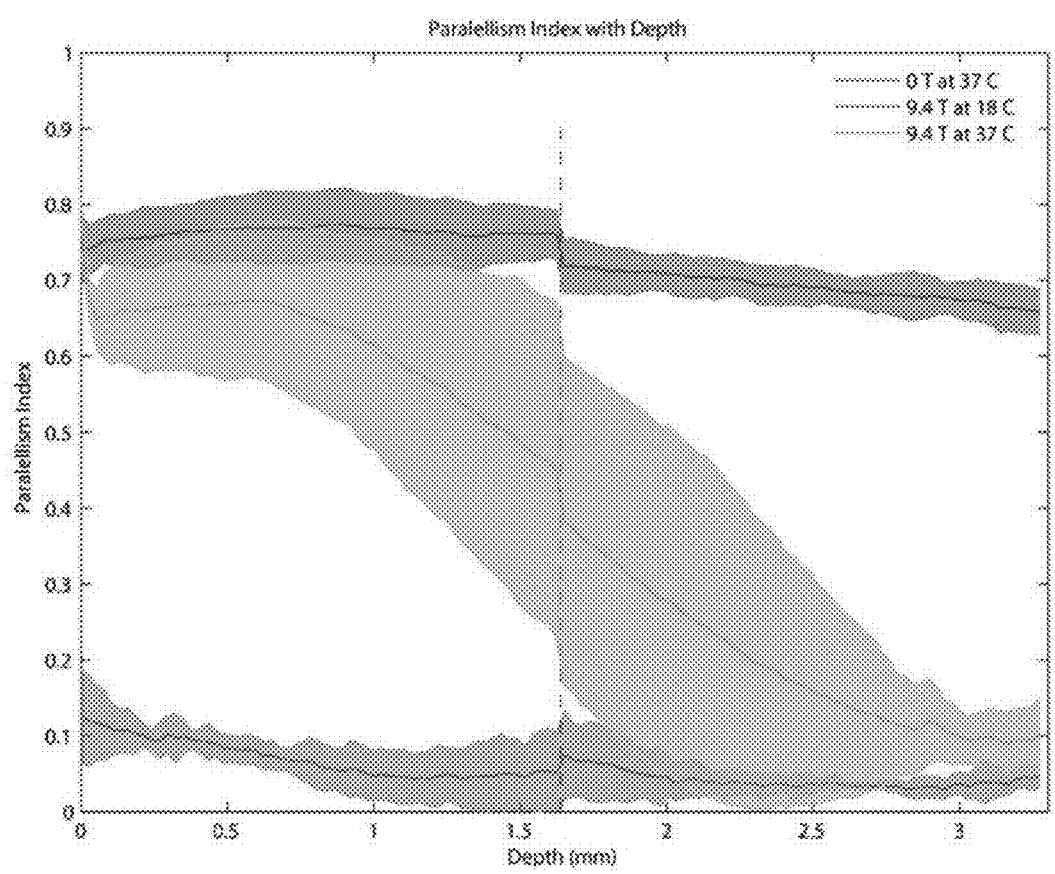
FIG. 16 depicts parallelism index versus depth of samples, according to exemplary embodiments of the present disclosure.
Figure 17:
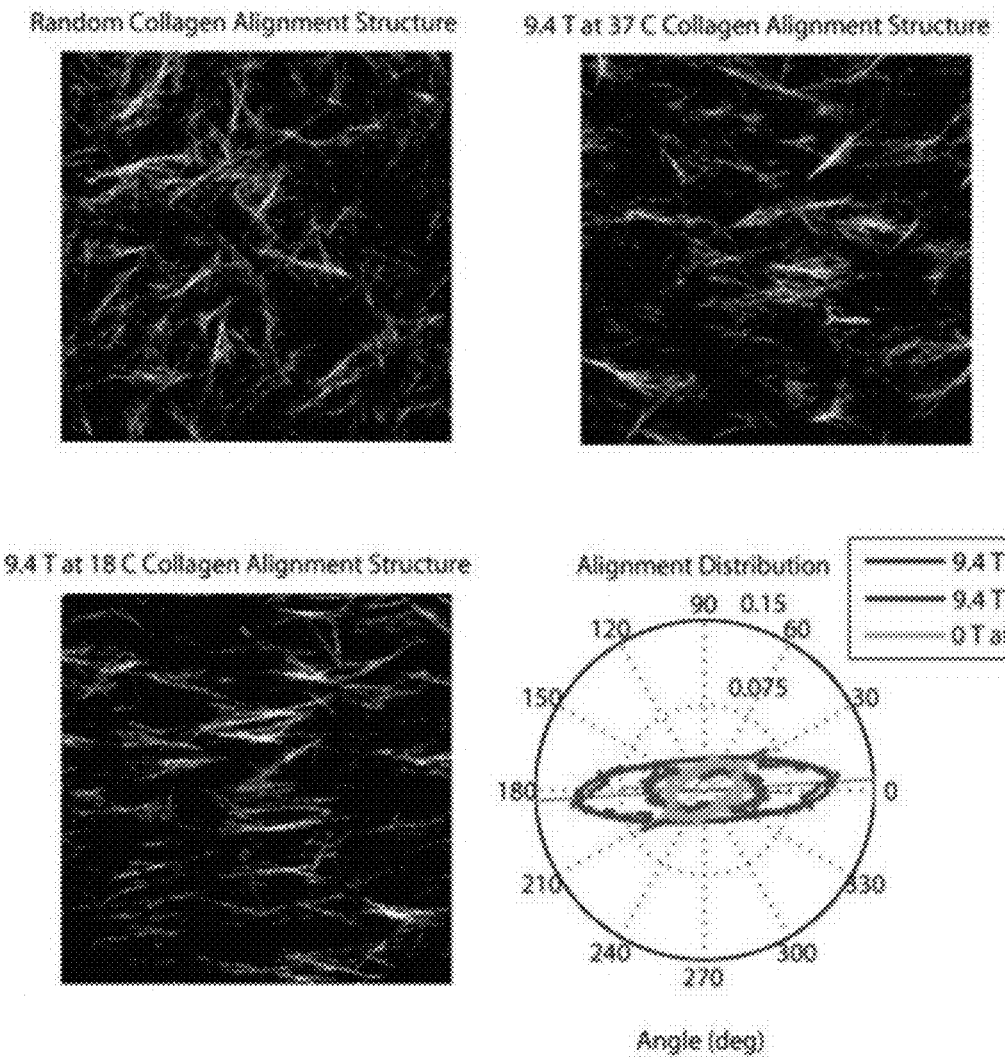
FIG. 17 depicts microscope images of three collagen samples and a corresponding angle distribution, according to exemplary embodiments of the present disclosure.

FIG. 16 demonstrates that the Parallelism Index, an indicator of birefringence, shows strong differences between collagen scaffold formed with and without a magnetic field. Scaffolds formed at 37° C. (lower line=0 T, diagonal middle line=9.4 T) within a magnetic field exhibit strong birefringence that diminishes through the depth of the gel. Fibrillogenesis at 18° C. (upper line) has markedly decreased this depth-dependent effect, allowing full thickness alignment of a collagen scaffold. FIG. 17 depicts that temperature manipulation during fibrillogenesis within a magnetic field shows qualitative and quantitative alignment microstructure under confocal microscopy. The upper left corner of FIG. 17 shows collagen gels formed outside of a magnet at 37° C., with random ultrastructure, while the upper right corner shows collagen formed at 37° C. within a magnetic field, showing only slight signs of alignment, requiring verification with quantitative analysis. The lower left corner of FIG. 17 shows collagen gels formed within a magnetic field at 18° C. with pronounced alignment, while the lower right corner shows collagen gels formed at 18° C. within a magnetic field exhibiting much tighter alignment distributions, as shown by Fast Fourier analysis. The widest outer oval represents 9.4 T at 18° C., the wide horizontal oval in the center represents 9.4 T at 37° C., and the angled innermost oval represents 0 T at 37° C.

Example 4

This example provides another demonstration of how modulation of temperature and collagen concentration influenced control of collagen fibril alignment by magnetic fields (MA). For this example, type I oligomeric collagen was polymerized over a temperature and concentration range (full factorial design for: 12° C., 18° C., 25° C., and 37° C., and 1, 3, and 5 mg/mL). Microscale fibril orientation was determined via confocal reflection microscopy. Fibril alignment (angle of alignment and degree of alignment) was assessed using 2D FFT (MATLAB). All data was statistically analyzed via one- and two-way ANOVA as appropriate including all main effects and interactions ($\alpha=0.05$).

With this example, fibril analysis revealed that MA, lower temperature, lower collagen concentration, and all interactions led to significant differences in aspect ratio ($p<0.001$). Additionally, it was found that MA ($p=0.049$), lower temperature ($p<0.001$), lower concentration ($p=0.009$), and all interactions ($p<0.028$) led to less variance of orientation angle.

Figure 18:
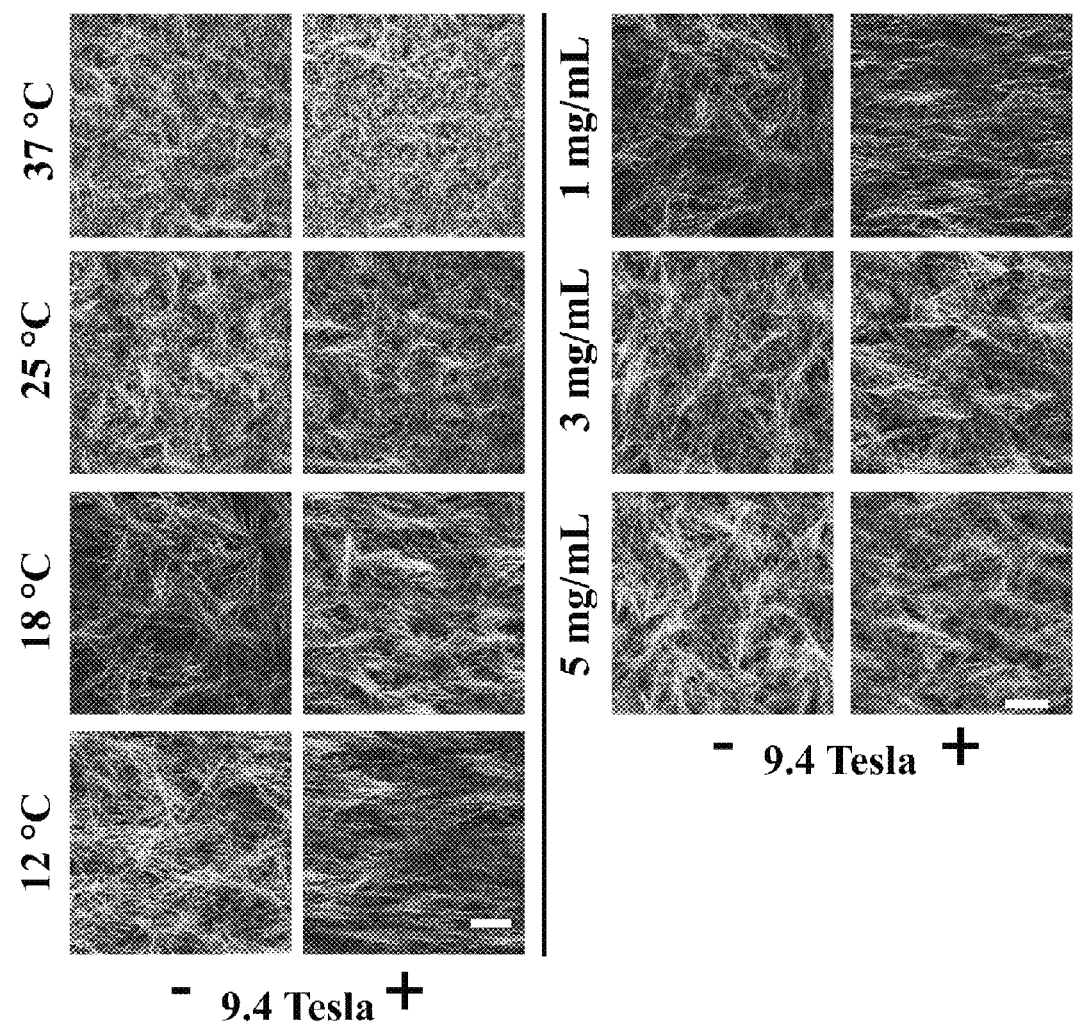
FIG. 18 depicts several microscope images of collagen samples with and without magnetic alignment at different temperatures, according to exemplary embodiments of the present disclosure.
Figure 19:
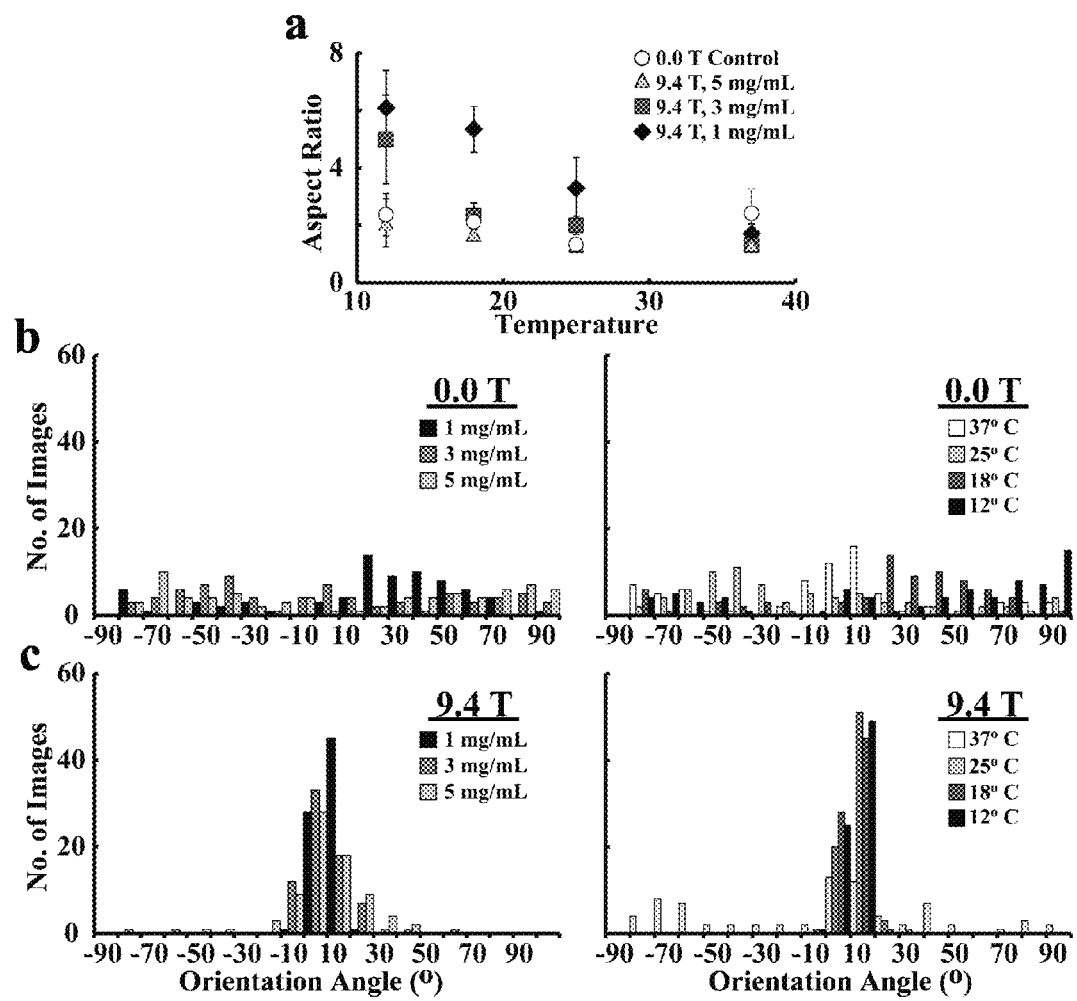
FIG. 19 depicts several charts showing that the aspect ratio increased (sub(a)) and the orientation angle decreased with decreased polymerization temperature and collagen concentration, at various concentrations without (sub(b)) and with (sub(c)) alignment and at various temperatures without (sub(d)) and with (sub(e)) alignment, according to exemplary embodiments of the present disclosure.

As shown in FIG. 18, collagen fibril alignment increased with decreased polymerization temperature and decreased collagen concentration (left side being constant concentration, right side being constant temperature). FIG. 19 shows that the aspect ratio increased and orientation angle variation decreased with decreased polymerization temperature and collagen concentration. In particular, FIG. 19 depicts several charts showing that the aspect ratio increased (sub(a)) and the orientation angle decreased with decreased polymerization temperature and collagen concentration, at various concentrations without (sub(b)) and with (sub(c)) alignment and at various temperatures without (sub(d)) and with (sub (e)) alignment.

This example further shows a control of fibril alignment higher than previously reported in the ability to control alignment in tissue thick samples, and also demonstrates advanced fibril control through temperature modulation, which expands the applicability of this method for tissue-engineered constructs.

Example 5

As generally referenced herein, primary challenge in the development of successful tissue-analogs is the emulation of the structural/mechanical properties, as well as the cell-matrix interactions of the native tissue. These properties serve to meet the environmental demands of a potential implant tissue and serve to support tissue-specific cellular viability, morphology, differentiation, and maturation. The present disclosure also includes disclosure of the magnetic alignment (MA) of collagen matrices with varying levels of hyaluronic acid (HA) would influence the compressive mechanical properties and bulk cell-matrix interaction using primary cells.

For the present example, 5 mg/mL oligomer collagen matrices were neutralized and mixed with 0, 1, 5, and 10 mg/mL HA. Matrices were polymerized at 18° C. in the presence or absence of a 9.4 Tesla magnetic field. After polymerization, collagen alignment was confirmed via FFT analysis. Hydrogels were tested in unconfined compression using a stress relaxation protocol (5% increments, 20% total strain, 30s hold time). Instantaneous and equilibrium moduli were measured from the acquired force and displacement data. Cell-induced contraction was also assessed over a 2-week time course. Primary bovine chondrocytes (fifth passage) were seeded at $1 \times 10^6$ cells/mL prior to polymerization. Cell viability determined via live/dead staining (calcein AM/propidium iodide). All data were analyzed via General Linear Model ANOVA incorporating all main effects and interactions as appropriate ($\alpha=0.05$, *=MA effect, ‡=HA effect).

Figure 20:
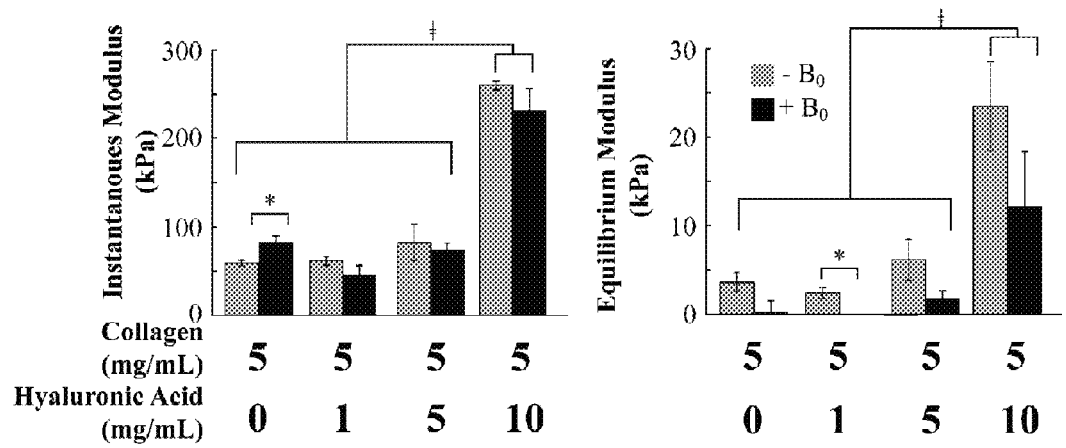
FIG. 20 depicts the instantaneous modulus and the equilibrium modulus for various collagen samples with and without hyaluronic acid, according to exemplary embodiments of the present disclosure.
Figure 21:
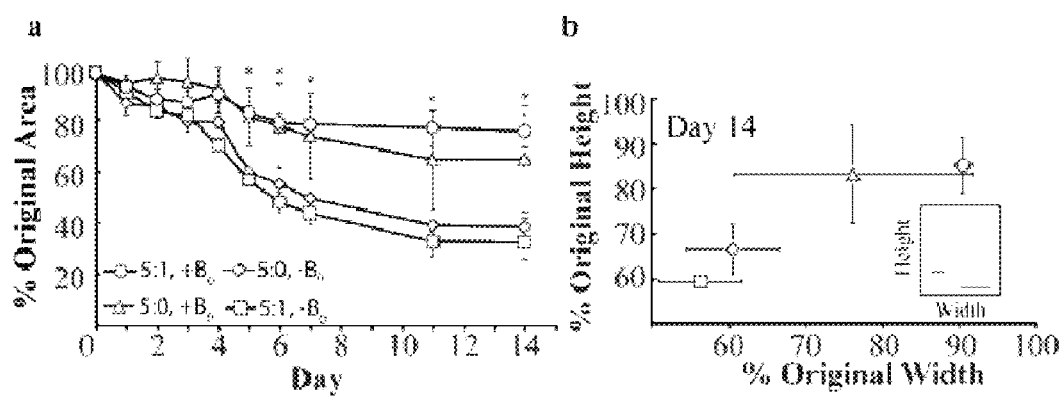
FIG. 21 depicts changes in area (sub(a)) and height and width (sub(b)) of various collagen and hyaluronic acid hydrogels over time, according to exemplary embodiments of the present disclosure.

For 5:0 and 5:1 mg/mL collagen:HA hydrogels, it was found that MA had a significant effect on compressive mechanical properties, as shown in FIG. 20. As shown in FIG. 20, MA ($+B_o$) and HA addition significantly affect bulk compressive mechanics. In cellularized scaffolds, it was found that MA, but not HA content, significantly reduced cell mediated contraction, as shown in FIG. 21 (where magnetically aligned collagen-HA hydrogels (X:Y) reduce cell-mediated contraction regardless of HA content). At day 5 and throughout the rest of the study, MA scaffolds were found to experience significantly lower cell-mediated contraction than unaligned scaffolds ($p<0.05$). Overall average cell viability of 91% on Day 1, qualitatively maintained throughout the study.

As generally referenced above, MA provides a nondestructive method to create aligned collagen hydrogels in 3D, including collagen-HA copolymer hydrogels. Aligned collagen fibrils create a unique mechanical microenvironment, altering the bulk and local mechanical properties as evidenced by the results. Collagen hydrogels can be fabricated with tailored properties for a variety of tissue engineering applications.

Example 6

In this example, a parameter space was established to carefully manipulate alignment of thick collagen matrices using a high strength magnetic field (9.4 Tesla). Temperature and concentration were manipulated to alter the alignment of the collagen microstructure. Collagen matrices were analyzed using polarized light microscopy for bulk analysis of alignment. Confocal reflection microscopy was used to analyze microscale fibril anisotropy. Full thickness alignment (~7 mm) was achieved using low temperatures (12° C. and 18° C.) and concentrations (1 and 3 mg/mL). The depth of alignment generally decreased with increasing temperature and concentration. Fibril anisotropy achieved standard deviations in alignment of 14.6° and 44.2° in constructs formed at 12° C. and 37° C., respectively. This work demonstrates a method to define anisotropy in large collagen-rich matrices through magnetic field, temperature, and concentration manipulation. The results also define parameters required to obtain desired homogeneous or gradient alignment profiles that are expected to be useful for a variety of biophysical and biomedical applications.

This example explores the parameter space associated with achieving high levels of anisotropy and controlling depth-dependent alignment of collagen scaffolds by magnetic fields. Initial screening of fibrillogenesis kinetics analyzed temperature with six levels (12° C., 15° C., 18° C., 20°

Figure 22:
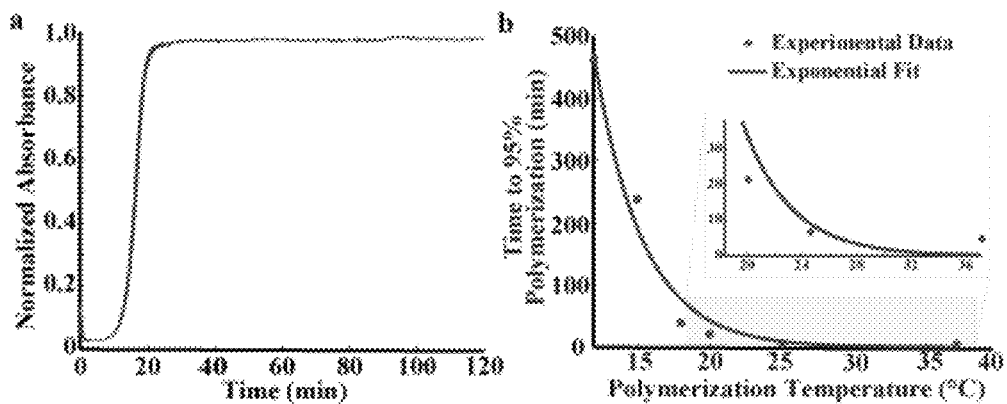
FIG. 22 depicts the normalized absorbance over time (sub(a)) and the time to 95% polymerization (sub(b)) at different temperatures for various collagen samples, according to exemplary embodiments of the present disclosure.

C., 25° C., and 37° C.). For alignment analysis factors of interest were magnetic field exposure with two levels (0.0 and 9.4 Tesla (T)), temperature with four levels (12° C., 18° C., 25° C., and 37° C.), and concentration with three levels (1, 3, and 5 mg/mL). Temperature levels were selected to include physiologically relevant magnitudes (i.e. 37° C., commonly used for fibrillogenesis of commercial sources) and lower levels that extend the fibrillogenesis time, as shown in FIG. 22. Collagen concentration levels were selected to span those typically used in tissue engineering applications. Control groups established the effect of temperature at 0.0 T using a concentration of 3 mg/mL, and the effect of concentration at 18° C. and 37° C. Magnetic field treatment groups included all concentration/temperature combinations (n=3 for all combinations, including among controls).

Type I oligomeric collagen was extracted to a concentration in the range of 6.0-7.0 mg/mL. Collagen was diluted and neutralized to the desired concentration of 1, 3, or 5 mg/mL using 0.01 N HCl, 1× phosphate buffered saline, 0.34 mM $CaCl_2$, and 0.01N sodium hydroxide.

Fibrillogenesis was monitored by a turbidity analysis performed using a Lambda 35 UV/Vis spectrophotometer system (Perkin Elmer; Waltham, Mass.) with an absorbance at 313 nm. Temperature was controlled using a refrigerated water-pump (Isotemp 3006D, Fisher Scientific). Fibrillogenesis kinetics were assessed at 3 mg/mL with six different temperatures: 12° C., 15° C., 18° C., 20° C., 25° C., and 37° C. Fibrillogenesis time was determined as the time to reach 95% of maximum absorbance.

Scaffolds were formed either within the isocenter of a 9.4 T CMX-400 NMR magnet (Chemagnetics) or in a refrigerated incubator (control group). Experimentally derived fibrillogenesis times (as shown in FIG. 22) were used to determine how long samples remained at the treatment temperature. As shown in FIG. 22, temperature manipulation allows control of collagen fibrillogenesis kinetics. Sub (a) of FIG. 22 shows a representative turbidity profile generated at 25° C., and sub(b) shows fibrillogenesis times, expressed as time to reach 95% maximum absorbance, follow a two-parameter exponential decay with increasing temperatures ($R2=0.9638$).

Scaffolds formed below 37° C. were successively raised to 37° C. for 1 hour following fibrillogenesis to assure full polymerization. Scaffolds were polymerized inside either three-dimensional printed chambers (accessible space 10×10×5 mm3, w×h×t) or within 10.61 mm×19 mm glass cylinders. When exposed to the magnetic field, the samples were expected to be oriented such that the direction of alignment is parallel to the base of the sample.

Figure 23:
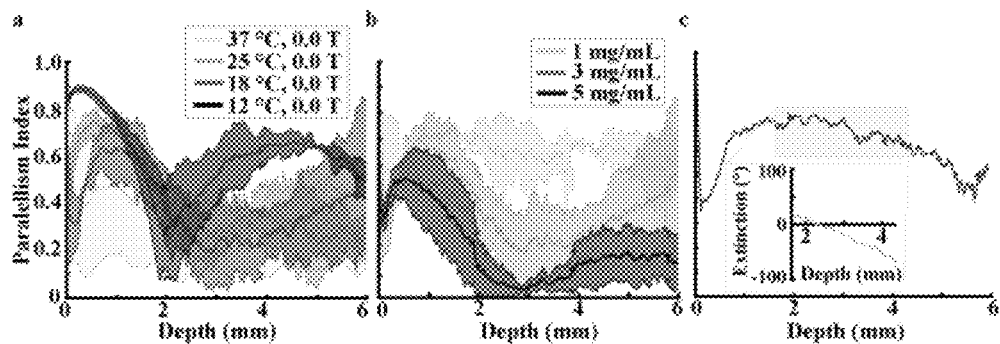
FIG. 23 depicts parallelism index information for control samples at various temperatures (sub(a)) and concentrations (sub(b)) and an inconsistent extinction angle throughout depth of a region of parallel index, according to exemplary embodiments of the present disclosure.

In addition to the foregoing examples and description, the present disclosure includes additional disclosure relating to collagen samples at various temperatures and concentrations. For example, FIG. 23 shows that control (random/unaligned) samples exhibit high variability when measured by polarized light microscopy. Control samples contain high variability in the parallelism index. In some cases control samples at various temperatures (sub(a)) and concentrations (sub (b)) may share similarities to aligned samples when viewed under polarized light microscopy. Sub(c) of FIG. 23 shows an inconsistent extinction angle throughout depth of a region of parallel index in a representative sample indicates a lack of uniform anisotropy.

Figure 24:
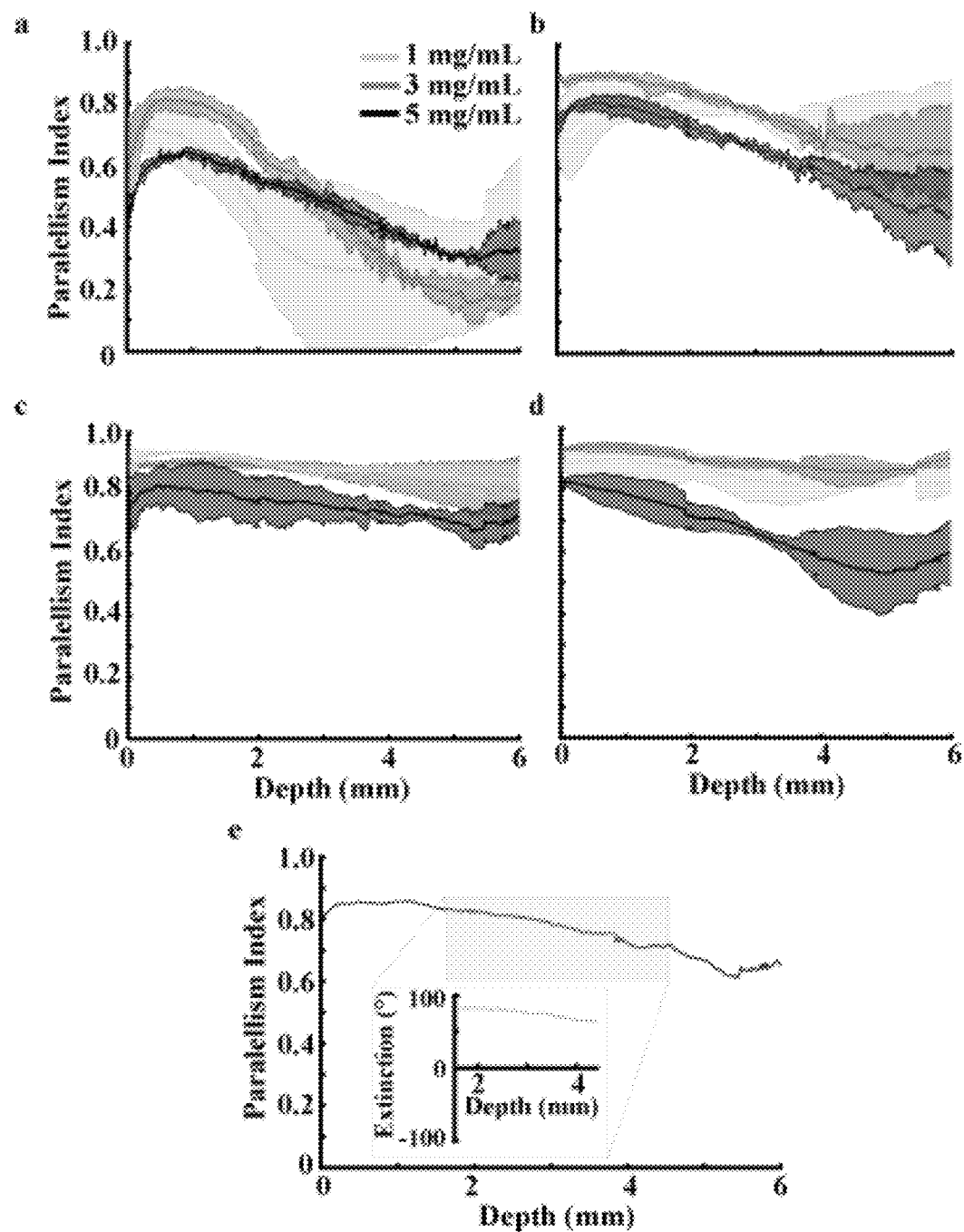
FIG. 24 depicts parallelism index curves for samples at 37° C. (sub(a)), 25° C. (sub(b)), and 18° C. (sub(c) and sub(d)), with a consistent extinction angle in an identified region (sub(e)), according to exemplary embodiments of the present disclosure.

FIG. 24 shows that the parallelism index calculated from polarized light microscopy allows quantification of alignment gradients in thick collagen scaffolds. Sub(a) of FIG. 24 shows that the Parallelism index (PI) at 37° C. is high near one end (0 mm) and drops throughout the depth of the collagen matrix. Sub(b) PI at 25° C. drops off at a slower rate throughout the collagen gel. Fibrillogenesis at 18° C. (sub(c) and sub(d)) aligns collagen throughout the gel thickness, represented by a constantly high PI. Sub(e) of FIG. 24 shows a consistent extinction angle in a region of a representative sample with high PI, indicating homogenous anisotropy.

Figure 25:
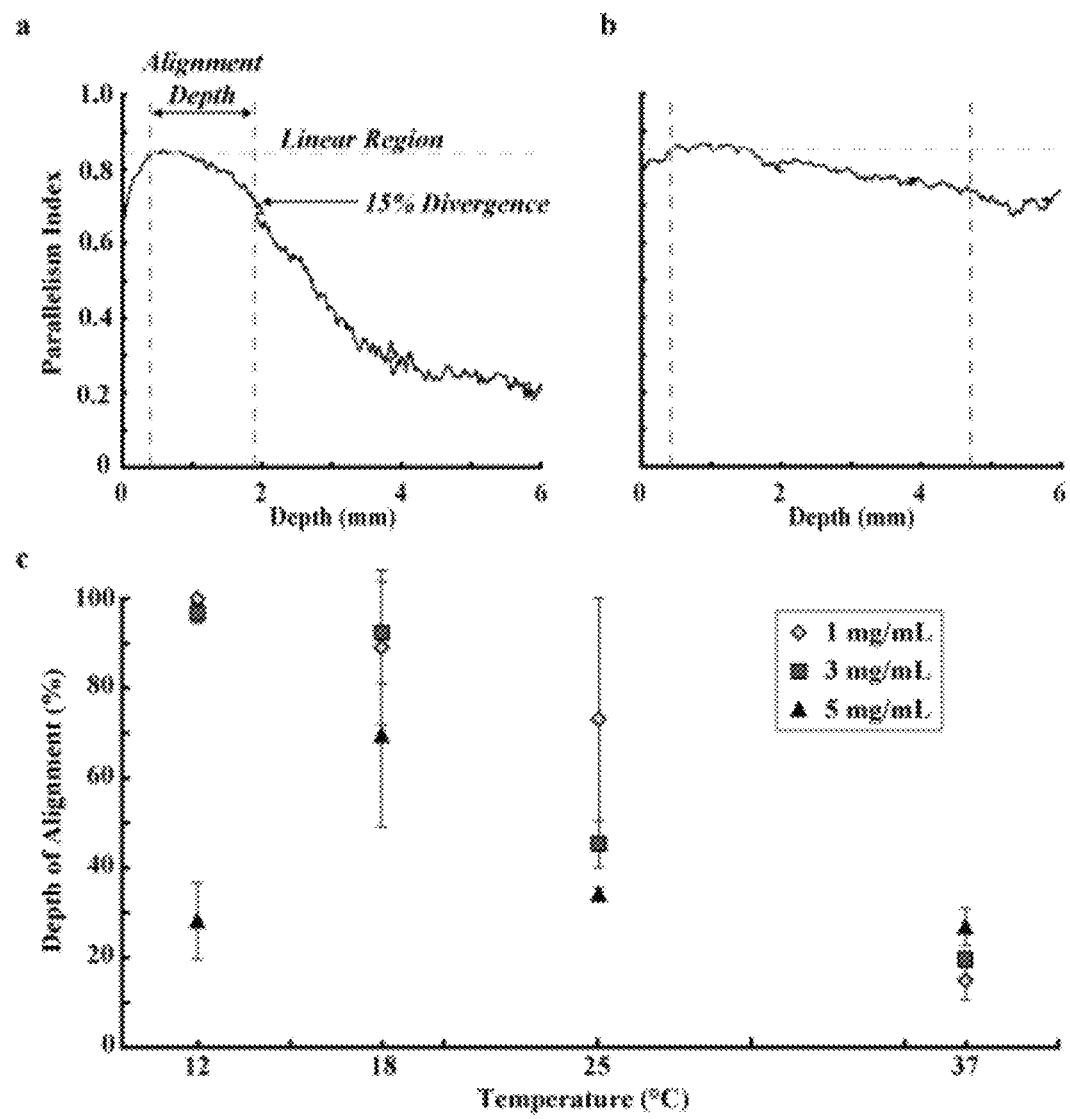
FIG. 25 depicts parallelism index curves for aligned samples at 37° C. (sub(a)) and 18° C. (sub(b)) and a chart showing depths of alignment at various temperatures (sub(c)), according to exemplary embodiments of the present disclosure.

FIG. 25 shows that polarized light microscopy allows calculation of alignment depth in aligned collagen gels. Alignment depth begins at the start of the linear region (first vertical dashed line) of the parallelism index (PI) graph and extends until the PI drops below a threshold amount (second vertical dashed lines). Collagen scaffolds formed in a 9.4 Tesla (T) magnet at 37° C. (sub(a)) exhibit much smaller depths of alignment when compared to scaffolds formed at 18° C. (sub(b)). Sub(c) of FIG. 25 shows that the depth of alignment is strongly affected by temperature and concentration ($p<0.0001$). Full thickness alignment is achieved at low temperatures (1° C., 18° C.), while higher temperatures (25°, 37° C.) allow control of gradient alignment profiles.

Figure 26:
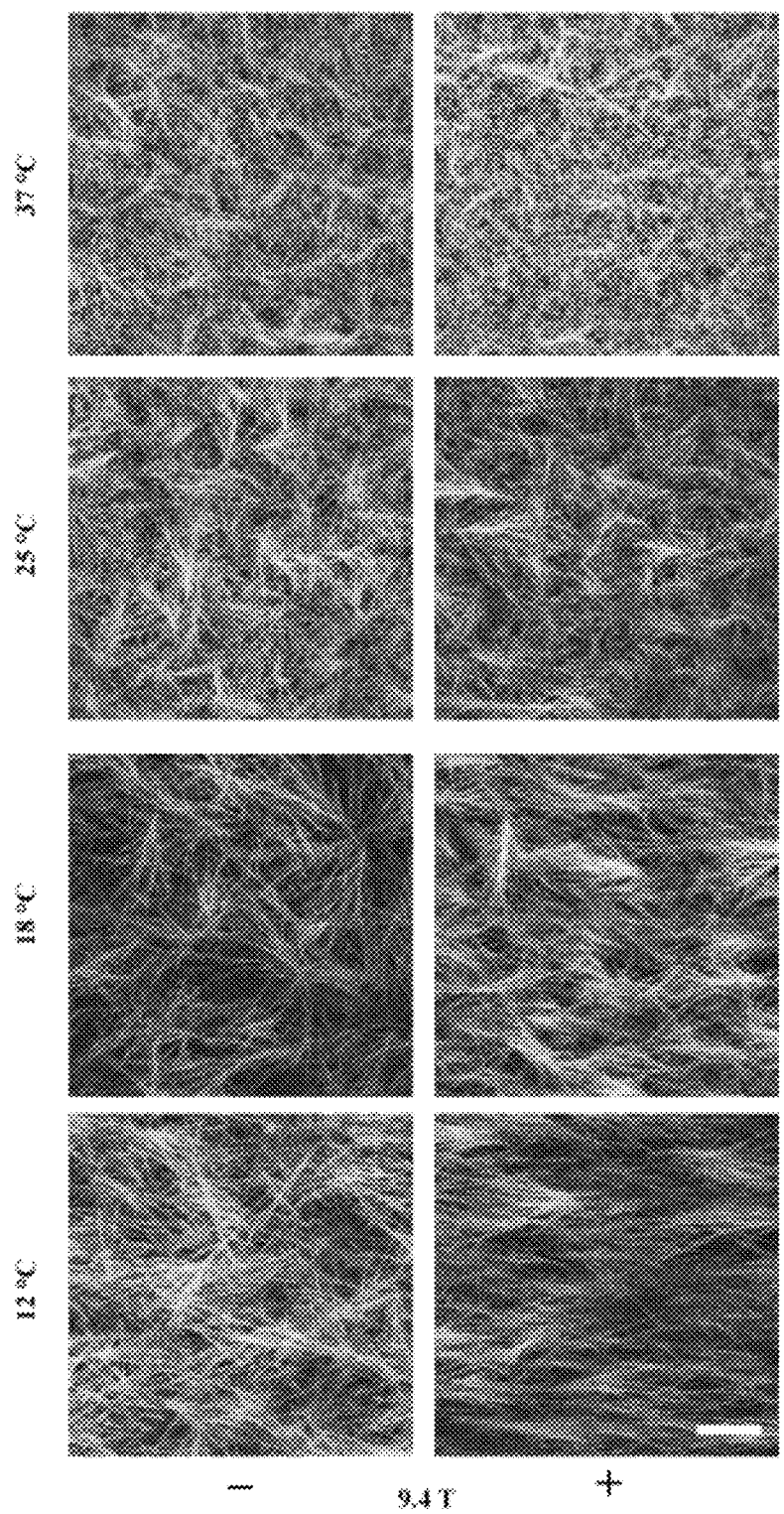
FIG. 26 depicts several microscope images of collagen samples at various temperatures, according to exemplary embodiments of the present disclosure.
Figure 27:
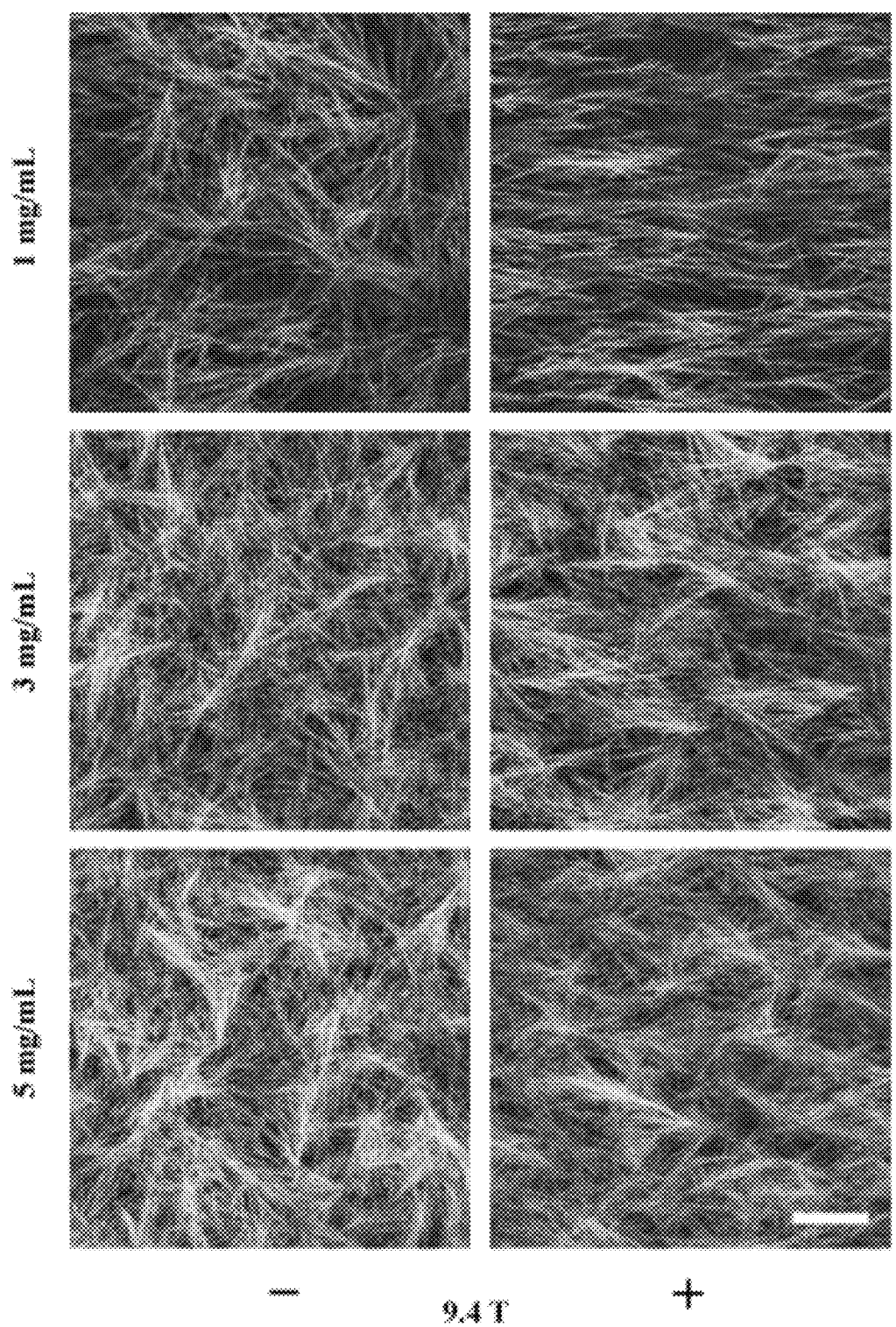
FIG. 27 depicts several microscope images of collagen samples at various concentrations, according to exemplary embodiments of the present disclosure.

FIG. 26 shows confocal reflection microscopy images revealing relationships between fibril anisotropy and fibrillogenesis temperature. Lower fibrillogenesis temperatures allow higher levels of anisotropy to be achieved when using high strength magnetic fields for collagen alignment. High polymerization temperatures (e.g. 37° C.) encourage formation of shorter fibrils, with frequent branching. The overall ultrastructure of the collagen matrix changes at lower temperatures (scale bar=60 μm). FIG. 27 shows confocal reflection microscopy images showing relationships between fibril anisotropy and collagen concentration. Collagen scaffolds formed at high concentrations in a magnetic field show lower levels of anisotropy than equivalent scaffolds at low temperatures (scale bar=60 μm).

Figure 28:
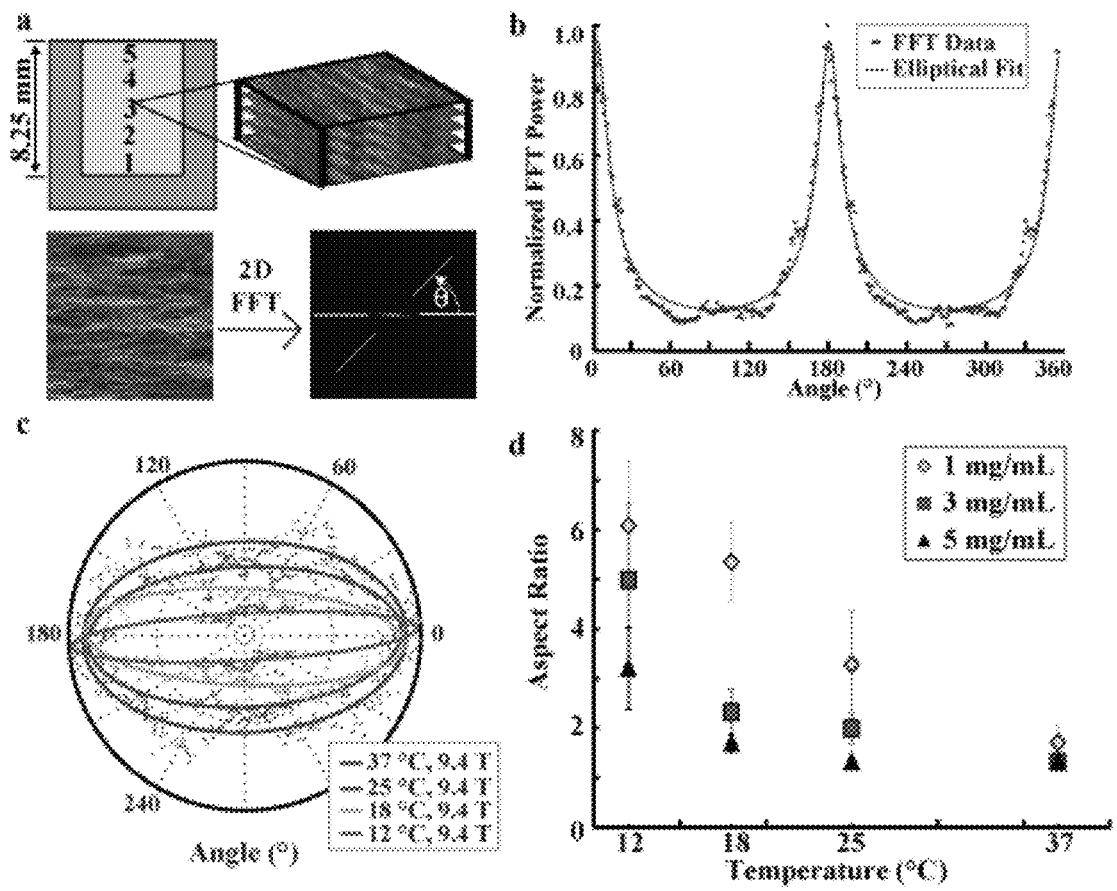
FIG. 28 depicts micrometer control allowing position controlled confocal (multislice) imaging through the scaffold depth (sub(a)), FFT power as a function of angle (°) fit with an ellipse using linear regression (sub(b)), polar plots allowing visualization of preferred fibril direction (sub(c)), and how aspect ratio is heavily influenced by fibrillogenesis temperature (sub(d)), according to exemplary embodiments of the present disclosure.

FIG. 28 shows how confocal microscopy allows for microscale analysis of collagen fibril alignment. Sub(a) of FIG. 28 shows micrometer control allowing position controlled confocal (multislice) imaging through the scaffold depth (8.25 mm). Images are taken at depths (1 through 5) that are spaced 1.9 mm apart. Images are then analyzed using a fast Fourier Transform (FFT). Image profiles are taken through the center of the 2D FFT in 5° increments to assess power in various directions. Sub(b) shows that FFT power as a function of angle (°) is fit with an ellipse using linear regression, with the peak of the ellipse representing the overall preferred orientation angle of the collagen fibril image. Sub(c) of FIG. 28 shows polar plots allowing visualization of preferred fibril direction. Samples formed at lower temperature demonstrate higher aspect ratios. Within sub(c), the oval rings, from the outer ring to the inner ring, represent 37° C., 25° C., 18° C., and 12° C., respectively. Sub(d) of FIG. 28 shows that the aspect ratio is heavily influenced by fibrillogenesis temperature ($p<0.0001$). Maximum aspect ratios are attained at lower fibrillogenesis temperatures. Higher concentration scaffolds exhibit lower aspect ratios ($p<0.0001$).

Figure 29:
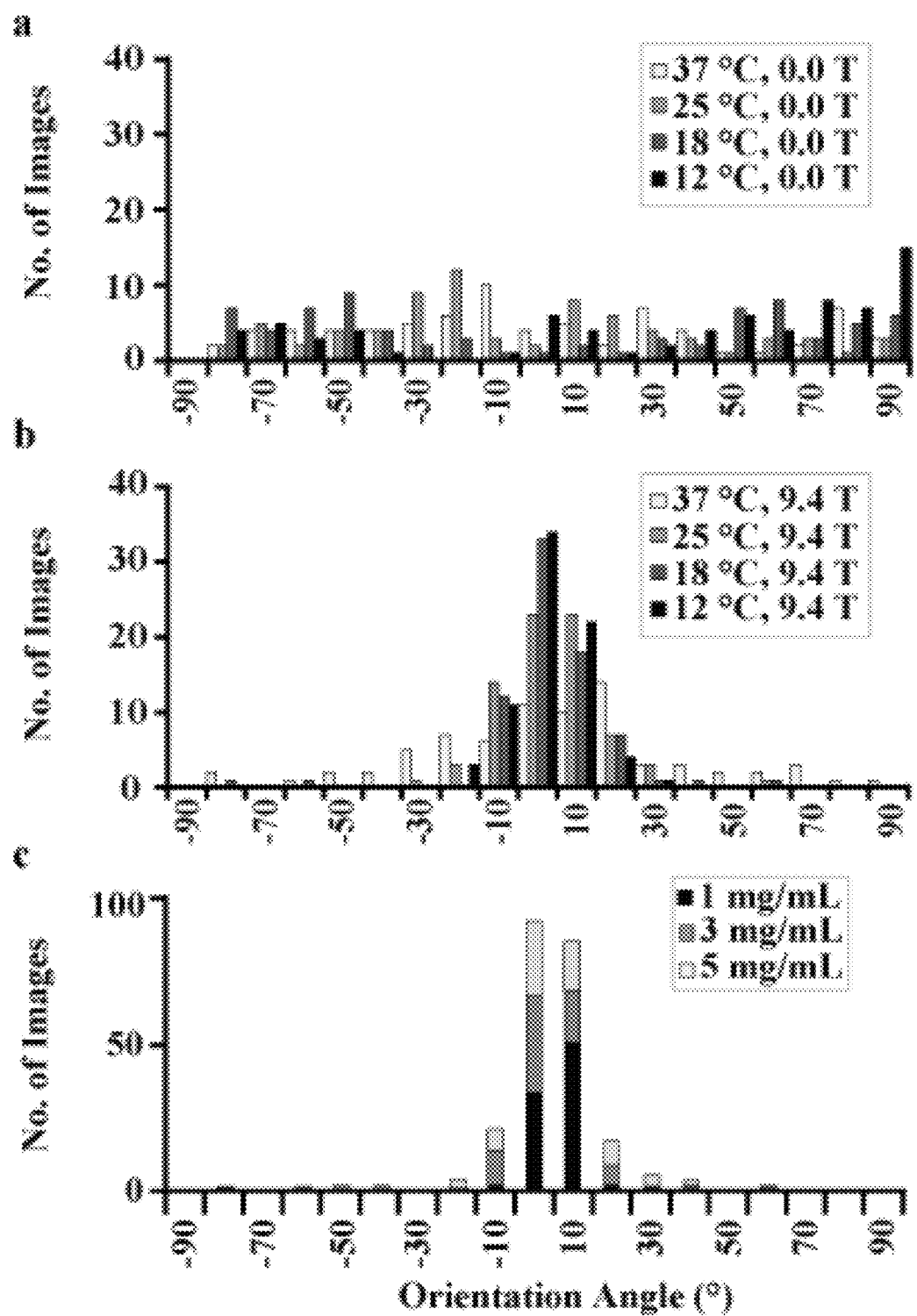
FIG. 29 shows histograms of preferred orientation angles across images obtained from various collagen scaffolds, at various temperatures without (sub(a)) and with (sub(b)) magnetic alignment and at different concentrations, according to exemplary embodiments of the present disclosure.
Figure 30A:
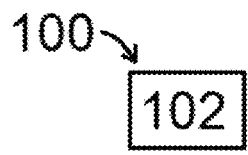
FIGS. 30A-31C show block diagrams of various exemplary constructs, according to exemplary embodiments of the present disclosure.
Figure 30D:
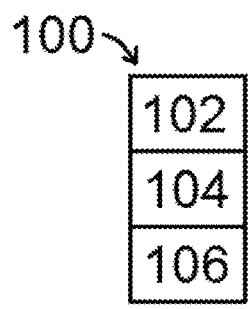
Figure 30G:
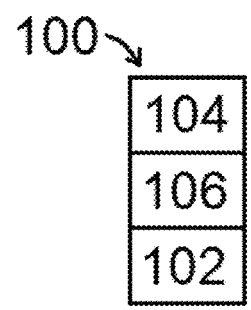
Figure 30B:
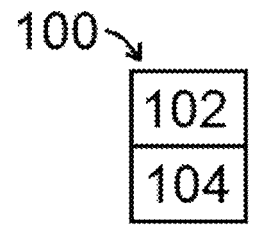
Figure 30E:
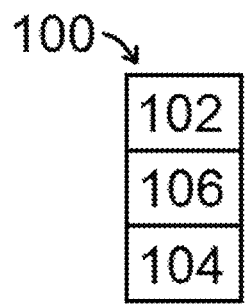
Figure 30H:
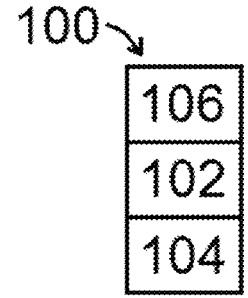
Figure 30C:
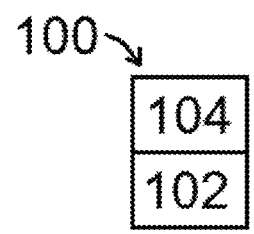
Figure 30F:
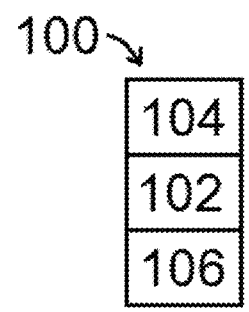
Figure 30I:
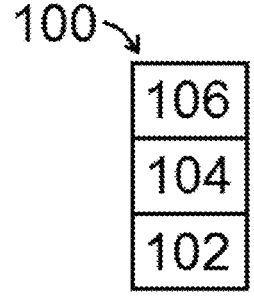

FIG. 29 shows histograms of preferred orientation angles across all images obtained from each collagen scaffold. Sub(a) of FIG. 29 depicts preferred orientation angles of control (random) scaffolds formed at 0.0 T are distributed uniformly. Sub(b) shows that scaffolds formed in a 9.4 T magnetic field have narrow preferred orientation angle distributions when polymerized at lower temperatures. Sub(c) of FIG. 29 shows that scaffolds formed at 18° C., 9.4 T have tight preferred orientation angle distributions; however, the majority of images aligned at 0° are from lower concentrations, most notably 1 mg/mL (darkest). Higher concentrations broaden the distribution.

Figure 31A:
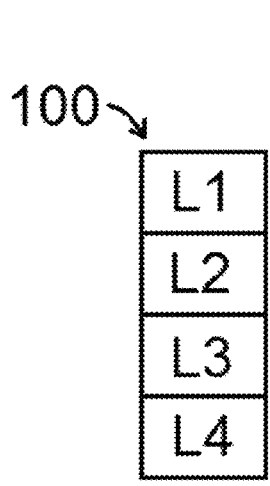
Figure 31B:
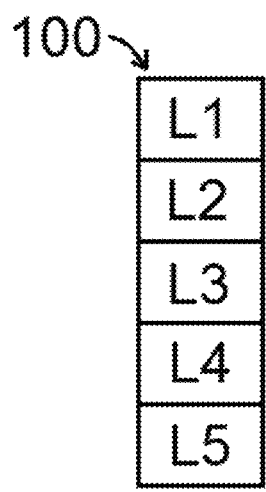
Figure 31C:
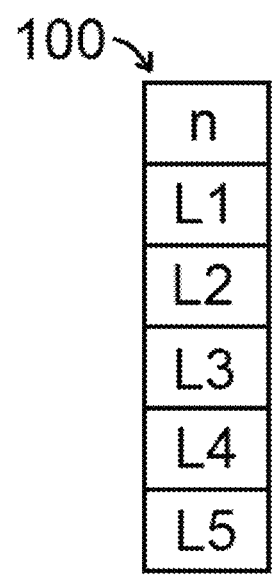

FIGS. 30A-31C show block diagrams of various exemplary constructs 100 of the present disclosure. Constructs 100 (which may be referred to as being and/or including various layers, or may also be referred to as being general products of the present disclosure) are shown in FIGS. 30A-30I as having one or more layers 102, 104, or 106, in various configurations relative to one another. For example, FIG. 30B shows layer 102 above layer 104, while FIG. 30C shows layer 104 above layer 102. The various layers 102, 104, and 106 may also be referred to herein as a first, second, and third layers, respectively. FIG. 31A-31C show exemplary constructs 100 of the present disclosure having four (FIG. 31A), five (FIG. 31B), or six or more (FIG. 31C) total layers. L1, L2, L3, L4 (in FIGS. 31A-31C) represent first, second, third, and fourth layers, while L5 (FIGS. 31B and 31C) represents a fifth layer. Layers L1, L2, L3, L4, and L5 are not limited to being in the relative order as shown in the figures, as they can be in any number of orders that can be contemplated, such as L3, L2, L5, L1, and L4, or L4, L1, L3, L5, and L2, or any number of other others. The lowercase "n" in FIG. 31C represents one or more additional layers, which can also be positioned in any number of orders in any number of times within constructs 100 of the present disclosure.

Multiple products can be produced based on MAP3D technology. First, a package can be a standalone unit and a non-cellularized scaffold for the repair of full cartilage defects. Second, the proposed package can be a standalone unit and aligned scaffold for the repair of partial cartilage defects and tissues with similar structure (e.g. skin). Third, the fabrication process can extend the ACT procedure for the incorporation of the patient's own autologous (e.g. primary or fat-/marrow-derived progenitor) cells in zonal scaffolds.

As referenced herein, and in various embodiments, applying an effective amount and/or level of temperature and/or magnetic range may be performed in connection with various layers, where effective amount means a desired range to generate a specific result. It is known that each instance will require a pre-determined temperature range and magnetic field to generate the desired results, which may also depend upon the type of organ/tissue being generated.

The method and product disclosed herein can improve on the techniques deployed presently in the art by providing a scaffold that closely resembles cartilage structure and function, and minimizes fibrocartilage formation. In addition, method and product disclosed herein can extend autologous chondrocyte transplantation through the introduction of a natural scaffold that closely resembles the native counterpart and serves as a carrier for cells and soluble factors.

Those skilled in the art will recognize that numerous modifications can be made to the specific implementations described above. Therefore, the subject matter disclosed above is not to be limited to the specific embodiments illustrated and described herein.

REFERENCES

1. Praemer, A. et al. Musculoskeletal conditions in the United States. *American Academy of Orthopaedic Surgeons* (1999).
2. Su, J. L. et al. Detection of superficial zone protein in human and animal body fluids by cross-species monoclonal antibodies specific to superficial zone protein. *Hybridoma* 20, 149-57 (2001).
3. Moutos, F. T. et al. A biomimetic three-dimensional woven composite scaffold for functional tissue engineering of cartilage. *Nat Mater* 6, 162-7 (2007).
4. Brittberg, M. et al. Treatment of deep cartilage defects in the knee with autologous chondrocyte transplantation. *N Engl J Med* 331, 889-95. (1994).
5. Reddi, A. H. Cartilage-derived morphogenetic proteins and cartilage morphogenesis. *Microsc Res Tech* 43, 131-6 (1998).
6. Neu, C. P. et al. Characterization of engineered tissue construct mechanical function by magnetic resonance imaging. *J Tissue Eng Regen Med* 3, 477-85 (2009).
7. Neu, C. P. et al. MRI-based technique for determining nonuniform deformations throughout the volume of articular cartilage explants. *Magn Reson Med* 53, 321-8 (2005).
8. Neu, C. P. et al. Mechanotransduction of articular cartilage superficial zone protein by TGF-b signaling. *Arthritis Rheum* 56, 3706-3714 (2007).
9. Neu, C. P. et al. The interface of functional biotribology and regenerative medicine in synovial joints. *Tissue Engineering, Part B: Reviews* (2008).
10. Diegmueller, J. et al. Modulation of hydroxyapatite nanocrystal size and shape by polyelectrolytic peptides. *Crystal Growth and Design*, in press (2010).
11. Luyten, F. P. et al. Recombinant bone morphogenetic protein-4, transforming growth factor-beta 1, and activin A enhance the cartilage phenotype of articular chondrocytes in vitro. *Exp Cell Res* 210, 224-9 (1994).
12. Khalafi, A. et al. Increased accumulation of superficial zone protein (SZP) in articular cartilage in response to bone morphogenetic protein-7 and growth factors. *J Orthop Res* 25, 293-303 (2007).
13. Mow, V. C. et al. Cartilage and diarthrodial joints as paradigms for hierarchical materials and structures. *Biomaterials* 13, 67-97 (1992).
14. Ramasamy, J. G. & Akkus, O. Local variations in the micromechanical properties of mouse femur: the involvement of collagen fiber orientation and mineralization. *J Biomech* 40, 910-8 (2007).
15. Dunn, G. A. & Ebendal, T. Contact guidance on oriented collagen gels. *Exp Cell Res* 111, 475-9 (1978).
16. Elsdale, T. & Bard, J. Collagen substrata for studies on cell behavior. *J Cell Biol* 54, 626-37 (1972).
17. Wilkinson, P. C. et al. Contact guidance of human neutrophil leukocytes. *Exp Cell Res* 140, 55-62 (1982).
18. Liao, S. et al. Biomimetic electrospun nanofibers for tissue regeneration. *Biomed Mater* 1, R45-53 (2006).
19. Zeugolis, D. I. et al. Electro-spinning of pure collagen nano-fibres—just an expensive way to make gelatin? *Biomaterials* 29, 2293-305 (2008).
20. Cheng, X. et al. An electrochemical fabrication process for the assembly of anisotropically oriented collagen bundles. *Biomaterials* 29, 3278-88 (2008).
21. Torbet, J. et al. Orthogonal scaffold of magnetically aligned collagen lamellae for corneal stroma reconstruction. *Biomaterials* 28, 4268-76 (2007).
22. Tranquillo, R. T. et al. Magnetically orientated tissue-equivalent tubes: application to a circumferentially orientated media-equivalent. *Biomaterials* 17, 349-57 (1996).
23. Pieper, J. S. et al. Crosslinked type II collagen matrices: preparation, characterization, and potential for cartilage engineering. *Biomaterials* 23, 3183-92 (2002).

24. Julkunen, P. et al. Biomechanical, biochemical and structural correlations in immature and mature rabbit articular cartilage. *Osteoarthritis Cartilage* 17, 1628-38 (2009).
25. Diekman, B. O. et al. Chondrogenesis of adult stem cells from adipose tissue and bone marrow: Induction by growth factors and cartilage derived matrix. *Tissue Eng Part A* (2009).
26. DuRaine, G. et al. Regulation of the friction coefficient of articular cartilage by TGF-beta1 and IL-1beta. *J Orthop Res* 27, 249-56 (2009).
27. Kon, E. et al. Orderly osteochondral regeneration in a sheep model using a novel nano-composite multilayered biomaterial. *J Orthop Res* 28, 116-24 (2010).
28. Kinner, B. & Spector, M. in *Methods of Tissue Engineering* (eds. Atala, A. & Lanza, R. P.) 1059-1073 (Academic Press, San Diego, Calif., 2002).
29. Breinan, H. A. et al. Effect of cultured autologous chondrocytes on repair of chondral defects in a canine model. *J Bone Joint Surg Am* 79, 1439-51 (1997).

The invention claimed is:

1. A method of generating an aligned collagen layer, comprising:
    applying a first magnetic field at or above 0.1 Tesla to a layer of a first collagen solution defining a horizontal plane, within a temperature at or between 2° C. and 45° C., to align a plurality of collagen fibrils formed within the first collagen solution before fibrillogenesis is complete and generate an aligned collagen layer having a planar fibril alignment and a thickness;
    selecting or altering the temperature as a tunable parameter to manipulate the rate of fibrillogenesis of the collagen fibrils to achieve a targeted degree of alignment of the collagen fibrils across the entirety of the thickness of the aligned collagen layer;
    combining the aligned collagen layer with a second layer of collagen, the second layer of collagen positioned adjacent to the aligned collagen layer to form a construct and comprising a quantity of collagen solution selected from a group consisting of a first quantity of a second collagen solution and a second quantity of the first collagen solution; and
    adding to the construct by combining the aligned collagen layer and the second layer of collagen with a third layer of collagen, the third layer of collagen positioned adjacent to one or both of the aligned collagen layer and the second layer of collagen and comprising a quantity of collagen solution selected from a group consisting of the first quantity of the second collagen solution, a second quantity of the second collagen solution, the second quantity of the first collagen solution, and a third quantity of the first collagen solution;
    wherein the temperature is tuned such that the step of applying takes longer than 30 minutes to achieve at least 95% fibrillogenesis of the collagen fibrils and at least one of the second and third layers of collagen of the construct consists of collagen fibrils that are randomly aligned.

2. The method of claim 1, wherein the step of applying is performed at a temperature of less than 20° C.

3. The method of claim 1, wherein:
    the step of applying is performed to align the collagen fibrils within the aligned collagen layer at an orientation angle range of at or between plus or minus 10°;
    the step of selecting or altering the temperature as a tunable parameter to manipulate the rate of fibrillogenesis comprises the steps of decreasing the rate of fibrillogenesis and delaying polymerization initiation.

4. The method of claim 1, wherein the first magnetic field is applied at a direction selected from the group consisting of a direction of the horizontal plane and a direction perpendicular to the horizontal plane; and
    the targeted degree of alignment of the collagen fibrils comprises a parallelism index of between 0.6 and 0.8 throughout the entirety of the thickness of the collagen layer.

5. The method of claim 1, wherein the step of combining further comprises the step of applying a magnetic field selected from the group consisting of the first magnetic field and a second magnetic field to the second layer of collagen to align collagen within the second layer of collagen relative to the selected magnetic field.

6. The method of claim 5, wherein the first magnetic field is at or about 90° relative to the second magnetic field.

7. The method of claim 1, wherein the step of adding to the construct further comprises the step of applying a magnetic field selected from the group consisting of the first magnetic field and the second magnetic field to the third layer of collagen to align collagen within the third layer of collagen relative to the selected magnetic field.

8. The method of claim 1, further comprising the step of:
    adding one or more additional layers of a collagen solution to the construct.

9. The method of claim 1, wherein:
    the first collagen solution comprises collagen and at least one substance selected from the group consisting of one or more minerals, one or more proteoglycans, hydroxyapatite, calcium, phosphorous, a combination of calcium and phosphorous, aggrecan, chondroitin sulfate, dermatan sulfate, genepin, hyaluronic acid, 1-Ethyl-3-(3-dimethylaminopropyl)carbodiimide, one or more cells, one or more primary mammalian cells, and one or more progenitor mammalian cells, and wherein the second collagen solution comprises collagen and is at least substantially free of the selected at least one substance; and
    the amount of the at least one substance in the first collagen solution is selected to achieve a desired effect on the fibril alignment of the aligned collagen layer.

10. The method of claim 1, further comprising the step of:
    administering at least the aligned collagen layer to a patient to treat a condition experienced by the patient, the condition selected from the group consisting of an arthritic condition, a cartilage-based condition, a bone-based condition, a ligament condition, and a tendon condition.

11. The method of claim 1, wherein the second layer of collagen consists of collagen fibrils that are randomly aligned and the second layer of collagen is positioned between the aligned layer of collagen and the third layer of collagen.

12. A method of treating a patient, comprising the step of:
    administering a construct to a patient to treat a patient condition, the construct formed by:
        forming a first layer of aligned collagen by applying a first direction magnetic field to a first quantity of a first collagen solution at a temperature of at or between 10° C. and 25° C. to align a plurality of collagen fibrils formed within the first collagen solution in a planar alignment relative to the first direction magnetic field before fibrillogenesis is complete;

selecting or altering the temperature as a tunable parameter to manipulate the rate of fibrillogenesis of the collagen fibrils to achieve a targeted degree of alignment of the collagen fibrils across the entirety of the thickness of the collagen layer, the temperature tuned such that the step of applying takes longer than 30 minutes to achieve at least 95% fibrillogenesis of the collagen fibrils;

combining the first layer of collagen with a second layer of collagen to form a construct, the second layer of collagen positioned adjacent to the first layer of collagen and comprising a quantity of a collagen solution selected from the group consisting of a first quantity of a second collagen solution and a second quantity of the first collagen solution; and adding one or more additional layers of a collagen solution to the construct, wherein at least one of the additional layers consists of collagen fibrils that are randomly aligned.

13. The method of claim 12, wherein the step of combining further comprises the step of applying a magnetic field selected from the group consisting of the first magnetic field and a second magnetic field to the second layer of collagen to align collagen within the second layer of collagen relative to the selected magnetic field.

14. The method of claim 12, wherein the step of adding one or more additional layers further comprises positioning a randomly aligned layer of collagen adjacent to the second layer of collagen.

15. The method of claim 14, wherein the second layer of collagen is positioned between the randomly aligned layer of collagen and the first layer of collagen.

16. A method of generating an aligned collagen layer, comprising:

applying a first magnetic field at or above 0.1 Tesla to a layer of a first collagen solution defining a horizontal plane, within a temperature at or between 2° C. and 45° C., to align a plurality of collagen fibrils formed within the first collagen solution before fibrillogenesis is complete and generate an aligned collagen layer having a planar fibril alignment and a thickness;

selecting or altering the temperature as a tunable parameter to manipulate the rate of fibrillogenesis of the collagen fibrils to achieve a targeted degree of alignment of the collagen fibrils across the entirety of the thickness of the aligned collagen layer;

crosslinking the aligned collagen layer, resulting in an individual aligned crosslinked collagen layer;

combining the aligned collagen layer with a randomly aligned layer of collagen, the randomly aligned layer of collagen consisting of collagen fibrils that are randomly aligned;

wherein the temperature is tuned such that the step of applying takes longer than 30 minutes to achieve at least 95% fibrillogenesis of the collagen fibrils.

17. The method of claim 16, further comprising the step of:

combining the aligned collagen layer with a second layer of collagen, the second layer of collagen comprising a quantity of a collagen solution selected from the group consisting of a first quantity of a second collagen solution and a second quantity of the first collagen solution;

wherein the second layer of collagen is positioned adjacent to the aligned collagen layer, forming a construct.

18. The method of claim 17, wherein the step of combining further comprises the step of applying a magnetic field selected from the group consisting of the first magnetic field and a second magnetic field to the second layer of collagen to align collagen within the second layer of collagen relative to the selected magnetic field.

19. The method of claim 17, further comprising the step of:

further combining the aligned collagen layer and the second layer of collagen with a third layer of collagen, the third layer of collagen comprising a quantity of a collagen solution selected from the group consisting of the first quantity of the second collagen solution, a second quantity of the second collagen solution, the second quantity of the first collagen solution, and a third quantity of the first collagen solution;

wherein the third layer of collagen is positioned adjacent to one or both of the aligned collagen layer and the second layer of collagen, adding to the construct.

20. The method of claim 17, wherein the randomly aligned layer of collagen is positioned between the aligned collagen layer and the second layer of collagen.

* * * * *